(12) United States Patent
Kowarz et al.

(10) Patent No.: US 7,274,454 B2
(45) Date of Patent: Sep. 25, 2007

(54) IMAGING SYSTEM WITH PROGRAMMABLE SPECTRAL SWITCH

(75) Inventors: Marek W. Kowarz, Henrietta, NY (US); James G. Phalen, Rochester, NY (US); J. Daniel Newman, Pittsford, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 11/316,857

(22) Filed: Dec. 23, 2005

(65) Prior Publication Data

US 2007/0146710 A1 Jun. 28, 2007

(51) Int. Cl.
- *G01N 21/25* (2006.01)
- *G02B 13/16* (2006.01)
- *G02B 27/14* (2006.01)
- *H04N 9/07* (2006.01)
- *H04N 5/225* (2006.01)

(52) U.S. Cl. ............... 356/416; 356/419; 348/335; 348/336; 348/339; 359/634

(58) Field of Classification Search ........ 356/319, 356/320, 332, 416, 419; 359/290–292, 634, 359/639, 640, 618; 382/162–167; 348/207.99, 348/335, 336, 339, 343, 344
See application file for complete search history.

(56) References Cited

U.S. PATENT DOCUMENTS

| | | | |
|---|---|---|---|
| 3,534,159 A * | 10/1970 | Eilenberger | 348/267 |
| 3,609,222 A * | 9/1971 | Howarth | 348/210.99 |
| 5,689,317 A | 11/1997 | Miller et al. | |
| 5,777,674 A * | 7/1998 | Ohmuro | 348/338 |
| 5,892,612 A | 4/1999 | Miller et al. | |
| 6,233,084 B1 * | 5/2001 | Owen et al. | 359/247 |
| 6,307,663 B1 | 10/2001 | Kowarz | |
| 6,411,425 B1 | 6/2002 | Kowarz et al. | |
| 6,507,326 B2 * | 1/2003 | Manabe et al. | 345/32 |
| 6,678,085 B2 | 1/2004 | Kowarz et al. | |
| 6,760,475 B1 | 7/2004 | Miller | |

OTHER PUBLICATIONS

U.S. Appl. No. 11/021,258, filed Dec. 21, 2004, Kowarz.
R.A. DeVerse, R.M. Hammaker, W.G. Fateley. "Realization of the Hadamard Multiplex Advantage Using a Programmable Optical Mask in a Dispersive Flat-Field Near Infra-Red Spectrometer", Applied Spectroscopy, vol. 54, No. 12, pp. 1751-1758.

* cited by examiner

*Primary Examiner*—Tarifur Chowdhury
*Assistant Examiner*—Daniel Cartoon
(74) *Attorney, Agent, or Firm*—Stephen H. Shaw

(57) ABSTRACT

An imaging apparatus has input optics for obtaining a multispectral image bearing light and a programmable spectral switching section. The programmable spectral switching section has a first lens for directing light toward a dichroic separator that separates the multispectral image bearing light into a plurality of discrete spectral bands, each directed to an optical switch. Each optical switch is selectively enabled to redirect its corresponding spectral band back through the first lens as switched spectral band light. A light path selector element directs switched spectral band light toward an image forming section that has a sensor lens for directing switched spectral band light toward an image sensor. The image sensor forms image data according switched spectral band light from each optical switch. A control logic processor communicates with optical switches and with the sensor, providing instructions for enablement of optical switches and obtaining sensor data.

37 Claims, 21 Drawing Sheets

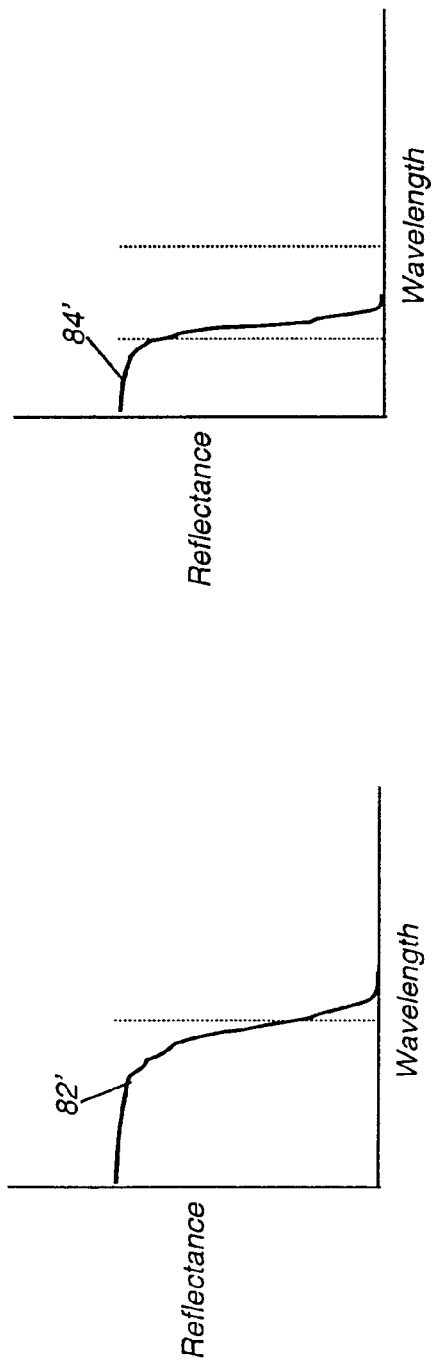
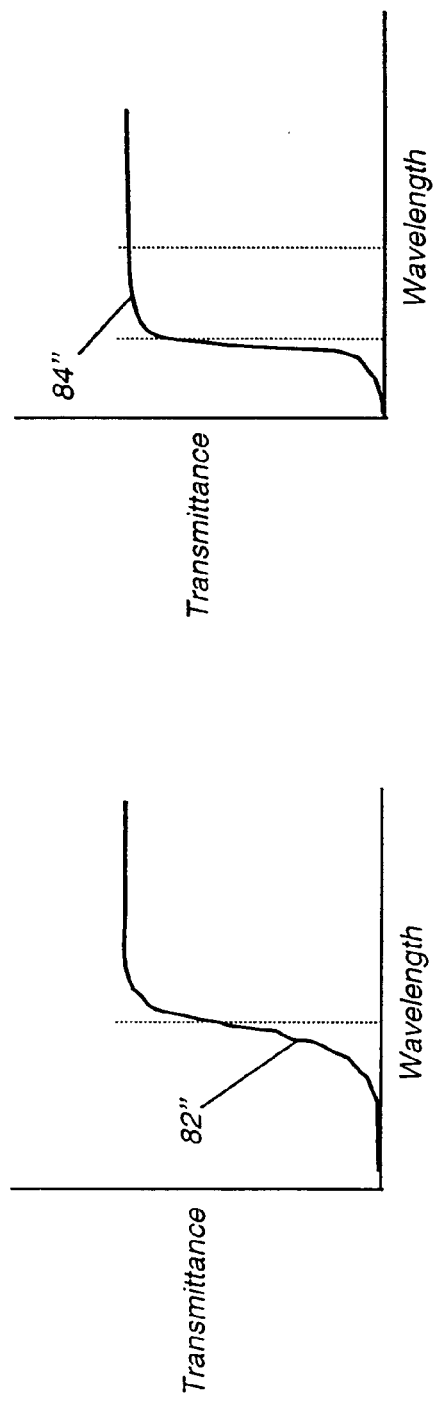
FIG. 8A
FIG. 8B
FIG. 8C
FIG. 8D

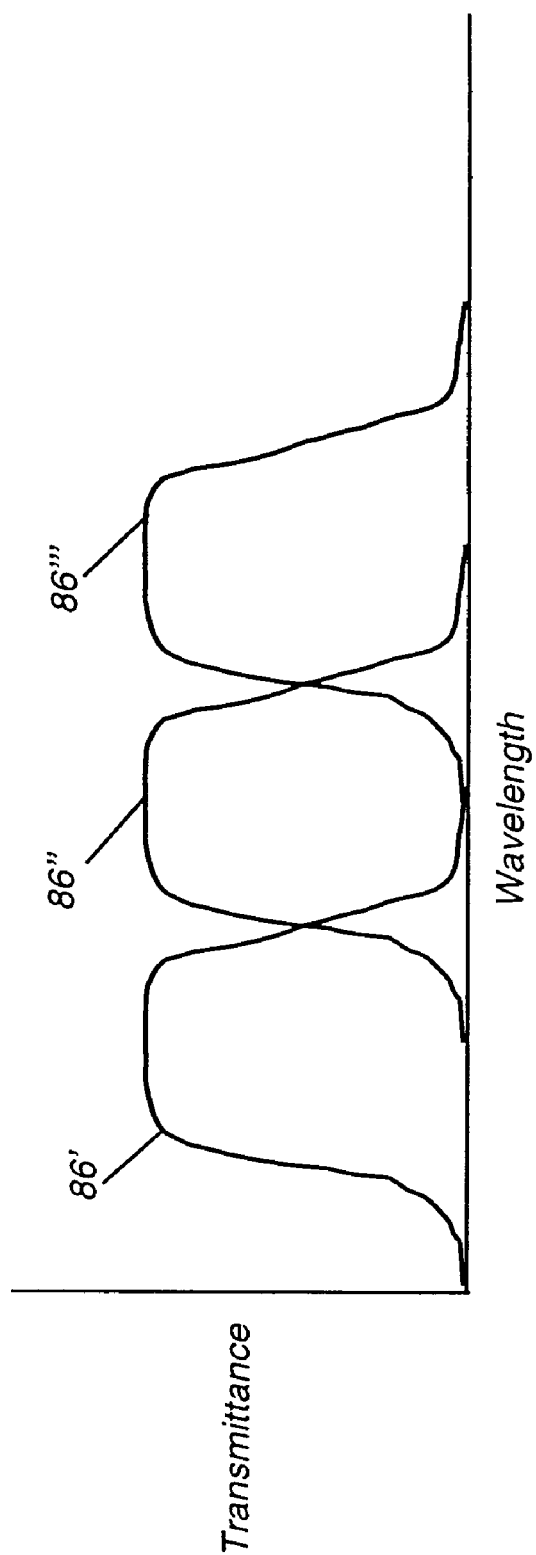

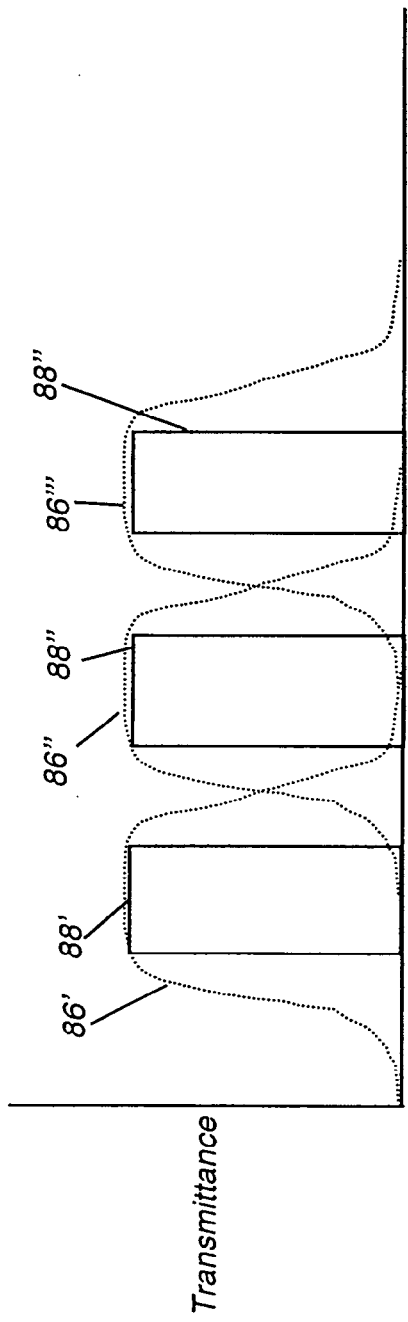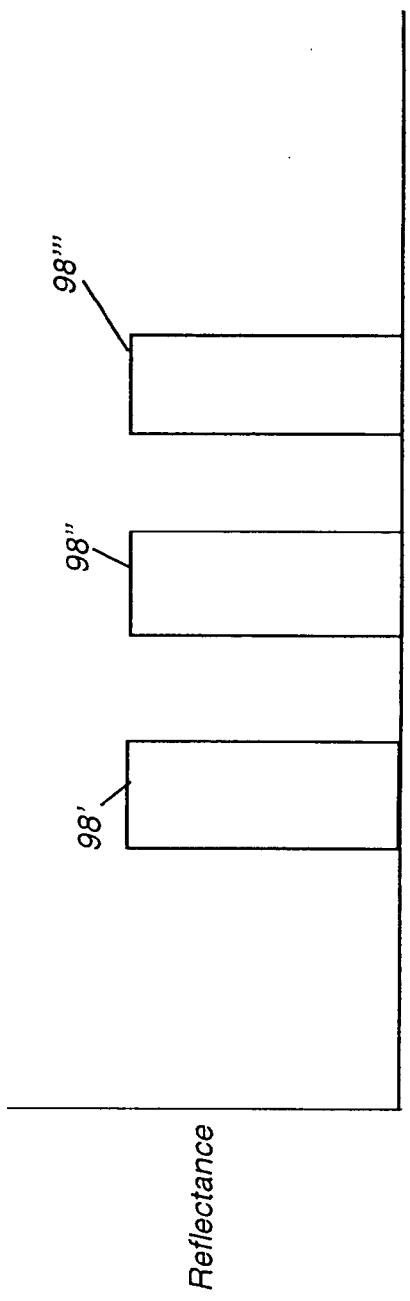

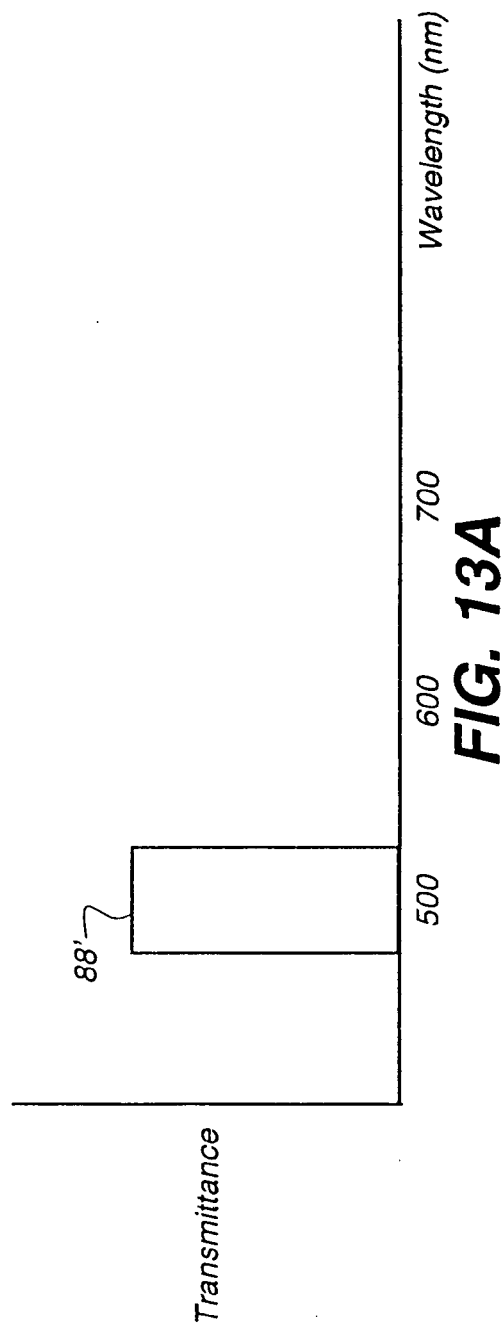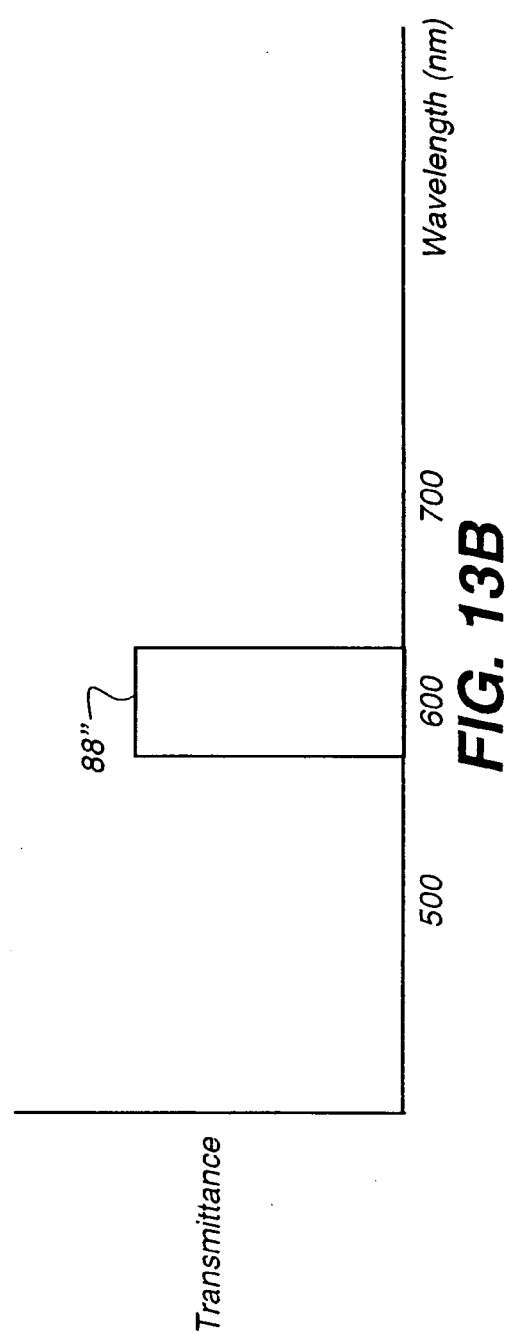

IMAGING SYSTEM WITH PROGRAMMABLE SPECTRAL SWITCH

FIELD OF THE INVENTION

The invention relates generally to imaging systems and in particular to a multi-band spectral imaging system employing light modulators for selection of spectral bands.

BACKGROUND OF THE INVENTION

There is significant interest in multi-spectral imaging (MSI) systems in which 3 or more bands of wavelengths can be captured by an imager for a variety of applications, including remote sensing, health imaging, and industrial sensing. MSI systems operate by capturing light from an object in a number of relatively narrow, discrete spectral bands and directing the light from each spectral band to an imaging sensor. MSI systems can be distinguished from HSI (Hyper-Spectral Imaging) systems that separate light from an object using dispersion to provide continuous spectral content, as contrasted with the discrete spectral bands used by the MSI system. An MSI system can employ any of a number of types of imaging sensors, including both area and linear sensors. Multi-spectral imaging systems can provide high-resolution spectral images of large, extended objects or areas with excellent image quality, short detector acquisition times, and manageable image data sets.

For MSI and related systems, it is necessary to provide some type of filtering mechanism for selecting spectral bandwidths of interest and blocking or attenuating unwanted spectral content. In one type of embodiment, an MSI system may use standard types of color filters, such as conventional dichroic filters, to perform this spectral selection function. Alternatively, various types of tunable transmission filters have been disclosed using liquid crystal (LC) devices, acousto-optical (AO) devices, and tunable Fabry-Perot cavities, for example. Liquid crystal tunable filters have been disclosed in U.S. Pat. No. 5,689,317 entitled "TUNABLE COLOR FILTER" to Miller et al. issued Nov. 18, 1997 and in U.S. Pat. No. 5,892,612 entitled "TUNABLE OPTICAL FILTER WITH WHITE STATE" also to Miller et al., issued Apr. 6, 1999. An imaging apparatus using tunable LC filters is disclosed in U.S. Pat. No. 6,760,475 entitled "COLORIMETRIC IMAGING SYSTEM" to Miller, issued Jul. 6, 2004.

While tunable LC filters provide an effective solution for some imaging applications, these devices have some significant limitations. These limitations include some constraints on spectral range, temperature sensitivity, polarization sensitivity, relatively poor transmission characteristics, and relatively slow response times.

One class of spectral imaging systems employs a spatial light modulator as a type of programmable spectral switch for directing each band of incident light obtained from an object field, in sequence, to a sensor. This approach has been demonstrated successfully for point-imaging and sensing apparatus that utilize a single detector element. However, it can be appreciated that there would be significant advantages to an imaging system in which the programmable spectral switch provides a programmable equivalent to a color filter wheel that would be compatible with both linear and area image sensors. For such a system, it would be particularly advantageous to use a spatial light modulator that is highly efficient, provides high contrast, and operates at high switching speeds. However, the performance requirements for spectral imaging with these devices exceed the capabilities of most types of spatial light modulators.

A particularly advantaged type of spatial light modulator is an electromechanical conformal grating device consisting of ribbon elements suspended above a substrate by a periodic sequence of intermediate supports, as disclosed by Kowarz in U.S. Pat. No. 6,307,663, entitled "Spatial Light Modulator With Conformal Grating Device" issued Oct. 23, 2001. The electromechanical conformal grating device is operated by electrostatic actuation, which causes the ribbon elements to conform around the support substructure, thereby producing a grating. The device of the '663 disclosure has become known as the conformal GEMS device, or more simply as the GEMS device, with GEMS standing for Grating ElectroMechanical System. The GEMS device possesses a number of attractive features. It provides high-speed digital light modulation with high contrast, high efficiency, and a relatively large addressable active region. Significantly, the GEMS device is designed for on-axis illumination, unlike other types of high-speed electromechanical light modulators, such as the Digital Micromirror Device™ (DMD) used in Digital Light Processor™ (DLP) systems manufactured by Texas Instruments, Inc., Dallas, Tex. As a further advantage, the GEMS device can be fabricated as a linear device with a thin active area, to modulate a thin line of an image at a time, or can be fabricated with a relatively wide active area in order to modulate a wider segment of an image at one time.

While there would be advantages to the use of GEMS and related devices, their deployment as spectral switches in a programmable spectral imaging system requires a different approach from the conventional use of these components in imaging and display systems.

SUMMARY OF THE INVENTION

The present invention is directed to addressing the need for a programmable spectral imaging system using GEMS devices as well as other types of linear and area spatial light modulators. The present invention provides an imaging apparatus comprising:

a) an input optics section for obtaining a multispectral image bearing light;

b) a programmable spectral switching section comprising:

a first lens for directing light along an optical axis and toward a dichroic separator, the dichroic separator separating the multispectral image bearing light into a plurality of discrete spectral bands, each spectral band directed to one of a plurality of optical switches;

each optical switch in the plurality of optical switches selectively enabled to redirect its corresponding spectral band along the optical axis and back through the first lens as switched spectral band light;

a light path selector element directing the switched spectral band light toward an image forming section;

c) the image forming section comprising a sensor lens for directing the switched spectral band light toward an image sensor;

the image sensor forming image data according to the switched spectral band light from each optical switch; and, d) a control logic processor in communication with the optical switches and with the image sensor, the control logic processor providing instructions for enablement of the optical switches and obtaining sensor data.

ADVANTAGEOUS EFFECT OF THE INVENTION

The present invention provides programmable spectral imaging system solutions that offer improved efficiencies, enhanced resolution, and excellent image quality.

It is a particular advantage of the apparatus of the present invention that, unlike conventional spectral imaging systems employing a color filter wheel for color separation, the present invention provides a programmable spectral imaging system without moving parts other than the micromechanical ribbon elements of the light modulator itself.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIGS. 8A through 8D are typical transmittivity graphs for dichroic surfaces in one embodiment;

FIG. 9 is a graph showing effective transmittivity for a typical X-cube in one embodiment;

FIGS. 10A and 10B are transmittivity graphs for a dichroic interleaver employed in one embodiment of the present invention;

FIGS. 13A, 13B, and 13C show a sequential approach for spectral band image capture, according to wavelength;

DETAILED DESCRIPTION OF THE INVENTION

The present description provides a programmable multiband spectral imaging system that employs spatial light modulators for selection of spectral bands. Where possible, the same numbering scheme has been employed throughout the figures for like components. It is to be understood that elements not specifically shown or described may take various forms well known to those skilled in the art.

Figure 1:
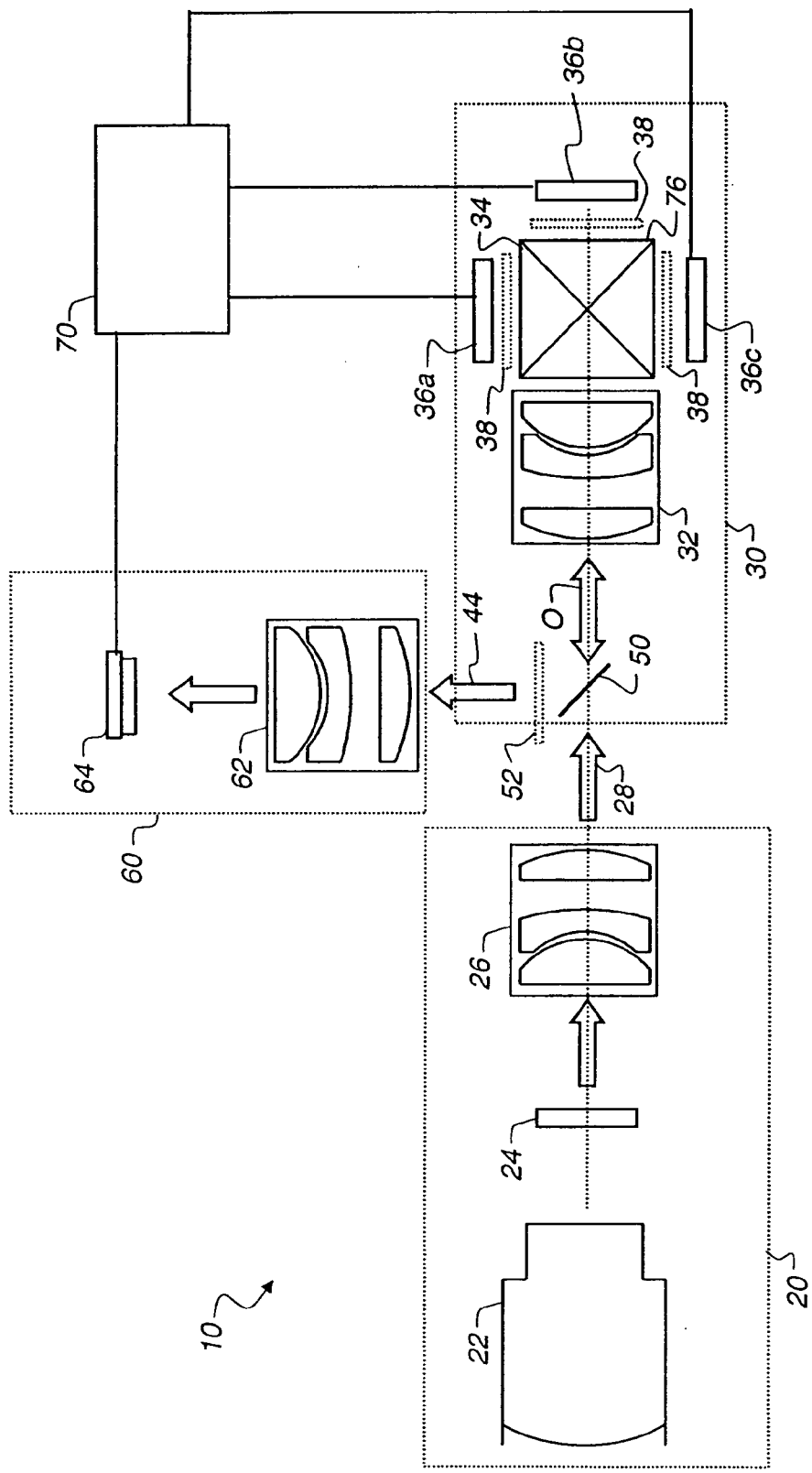
FIG. 1 is a schematic block diagram of a spectral imaging system according to one embodiment of the present invention.

Referring to FIG. 1, there is shown an exemplary embodiment of an imaging apparatus 10 according to the present invention. An input optics section 20, having forward optics 22 and a lens 26, directs an incident multispectral image bearing light 28 to a spectral switching section 30. Within spectral switching section 30, a patterned mirror 50, or other light path selector element, passes multispectral image bearing light 28 along an optical axis O toward a lens 32. Lens 32 then directs multispectral image bearing light 28 to a dichroic separator 34. Dichroic separator 34 functions as a spectral band separator and separates multispectral image bearing light 28 into two or more discrete spectral bands, each spectral band having a range of continuous, defined wavelengths.

Using a conventional approach for spectral imaging, each spectral band could be directed to a separate sensing element, obtaining the spectral data directly at each sensing element. With such an arrangement, however, multiple imaging sensors must be provided, i.e., one for each spectral band. For high-resolution imaging, a considerable amount of data would then be collected at each of the sensors and would need to be transferred, stored, and processed in order to provide the desired spectral data. While such a conventional approach can provide a workable solution, using this approach can result in considerable cost and complexity.

The apparatus of the present invention provides a spectral imaging solution having simplified data path requirements and using only a single image sensor. Referring again to FIG. 1, each spectral band is directed to one of a number of optical switches 36a, 36b, 36c. Each optical switch 36a, 36b, 36c is switched by a control logic processor 70 to redirect its corresponding spectral band, as a switched spectral band light 44, back toward patterned mirror 50 and toward an image sensor 64. The switched spectral band light 44 from each optical switch 36a, 36b, 36c is recombined along a common optical path, here, along optical axis O. Patterned mirror 50, serving as a light path selector, redirects this recombined switched spectral band light 44 to an image forming section 60. Image forming section 60 has a sensor lens 62 that directs the incident switched spectral band light 44 to image sensor 64. Image sensor 64 then provides image data corresponding to the intensity of switched spectral band light 44 that is received.

In input optics section 20, forward optics 22 typically has a number of lenses or mirrors that collect the light from the object field. In the specific embodiment shown in FIG. 1, forward optics 22 forms an intermediate image 24 as an object of lens 26. Lens 26 may be a single lens or may be a more complex lens assembly.

In the embodiment of FIG. 1, spectral switching section 30 employs GEMS devices as optical switches 36a, 36b, and 36c. Following the traditional color imaging model, optical switches 36a, 36b, and 36c switch light in red, green, and blue wavelengths, respectively; of course, alternative wavelengths of light may be switched in spectral switching section 30. Each optical switch 36a, 36b, 36c may be provided with an optional spectral clean-up filter 38 or trim filter that may be an absorption filter or dichroic filter, for example. Control logic processor 70 can switch one of optical switches 36a, 36b, and 36c at a time, to redirect one wavelength band of light as switched spectral band light 44. Alternatively, two or more optical switches 36a, 36b, 36c may be activated at one time, thereby simultaneously selecting multiple wavelength bands.

The behavior of GEMS devices and systems is described in considerable detail in commonly assigned U.S. Pat. No. 6,307,663, described above; in commonly assigned U.S. Pat. No. 6,411,425 entitled "Electromechanical Grating Display System With Spatially Separated Light Beams"; and in commonly assigned U.S. Pat. No. 6,678,085 entitled "High-Contrast Display System With Scanned Conformal Grating Device" all to Kowarz et al., the applicable parts of which are herein incorporated by reference.

In the embodiment of FIG. 1, dichroic separator 34 is an X-cube. Familiar to those skilled in the electronic color imaging arts, the X-cube typically consists of a crossed pair of dichroic surfaces that selectively reflect red and blue light components and transmit the green light component in conventional configurations. When configured using GEMS devices, each optical switch 36a, 36b, and 36c either reflects or diffracts the incident spectral band. Reflected light, or zeroeth order light, travels back along the optical axis O toward input optics section 20. Imaging light, consisting of at least one of the diffracted orders ( . . . –2, –1, 1, 2, . . . ) is off-axis with respect to the reflected zeroeth order light and is thus redirected by patterned mirror 50 or other type of light path selector.

In the embodiment shown in FIG. 1, lenses 26, 32, and 62 have the same focal lengths and thus provide unity magnification between the input image, images formed on optical switches 36a, 36b, and 36c, and the image formed on image sensor 64. However, it will be apparent to one skilled in the imaging arts that programmable spectral imaging apparatus 10 could alternatively have non-unity magnification, or even anamorphic magnification between any of the image planes. For example, one may alter the design of sensor lens 62 in order to provide anamorphic magnification at image sensor 64 or in order to change the f/# of imaging optics for forming an image at image sensor 64.

Lens 32 is preferably telecentric. Telecentric light is deemed sufficient for handling by dichroic surfaces such as those of X-cube 76. As is widely recognized, dichroic coatings reflect and transmit light as a function of incident angle and wavelength. As the incident angle varies, the wavelength of light that is transmitted or reflected also changes. Providing telecentric light minimizes these effects. Telecentric light is also preferred for modulation by GEMS devices in order to separate diffracted orders and simplifies alignment of optical switches 36a, 36b, and 36c. Furthermore, when GEMS devices are used as optical switches 36a, 36b, and 36c, it is preferable to position them so that intermediate images are formed near the GEMS device surface. It can be appreciated by those skilled in the imaging arts that the best arrangement for obtaining spectral image data is to form the optical image at the GEMS device surface itself.

Dichroic surfaces can be designed to obtain wavelength bands of interest and reject unwanted wavelengths with a high degree of accuracy. Dichroic surfaces can even be designed with multiple passbands and with variable transmission over a range of wavelengths, so that fairly complex response patterns can be obtained. However, any solution using dichroic surfaces is fixed to a specific filter pattern once it is fabricated.

Figure 2B:
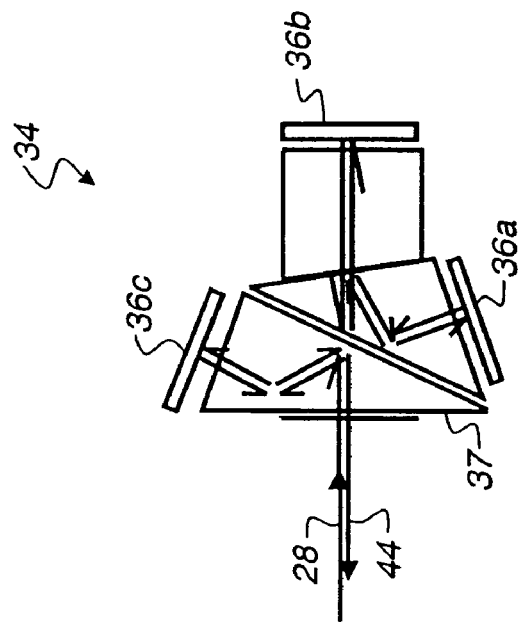
FIG. 2B is a block diagram showing a Philips prism used for wavelength separation.
Figure 2A:
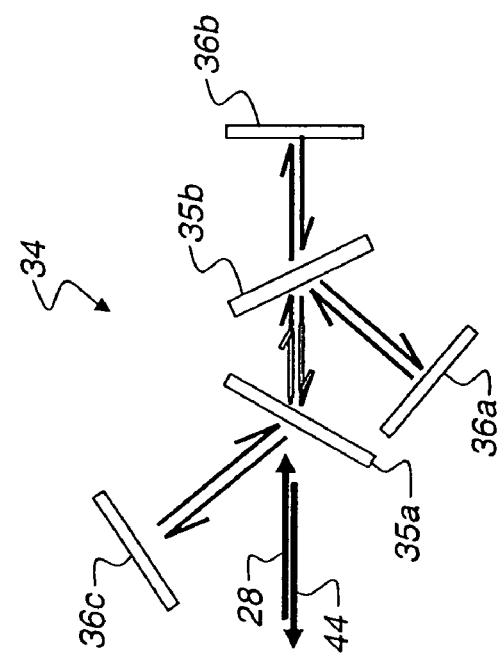
FIG. 2A is a block diagram showing an arrangement of dichroic plates for wavelength separation.

While the X-cube provides one type of solution for color separation, there are a number of alternative embodiments that may perform the function of dichroic separator 34 in an improved manner. As shown in FIG. 1, dichroic separator 34 accepts multispectral image bearing light 28 and separates it into various spectral bands. Dichroic separator 34 also recombines switched spectral band light 44 from each of the optical switches. Referring to FIG. 2A, there is shown an arrangement of dichroic plates 35a and 35b that could be used as one alternative to the X-cube. FIG. 2B shows a Philips prism 37 that could also serve as an alternative for dichroic separator 34. Both of the configurations shown in FIGS. 2A and 2B are advantaged over X-cube configurations, tending to be less polarization sensitive than arrangements using the X-cube. In addition, the configurations of FIGS. 2A and 2B do not exhibit the discontinuity that occurs in the middle of the field within the X-cube.

Image sensor 64 can be a device of one of a number of types, including a linear detector array, a multi-linear array, a time-delayed integration (TDI) linear array, or an area array. For visible and near-IR wavelengths, an exemplary type of detector array is a Charge-Coupled Device (CCD) or Complementary Metal Oxide Semiconductor (CMOS) device, components that are commonly used in digital cameras, document scanners, and other imaging equipment. When imaging apparatus 10 is configured in a line-scanned mode for use in a low-signal environment, the image sensor 64 array is preferably a time-delayed integration linear array. This time-delayed integration is then coordinated and temporally synchronized with line scanning.

Figure 3A:
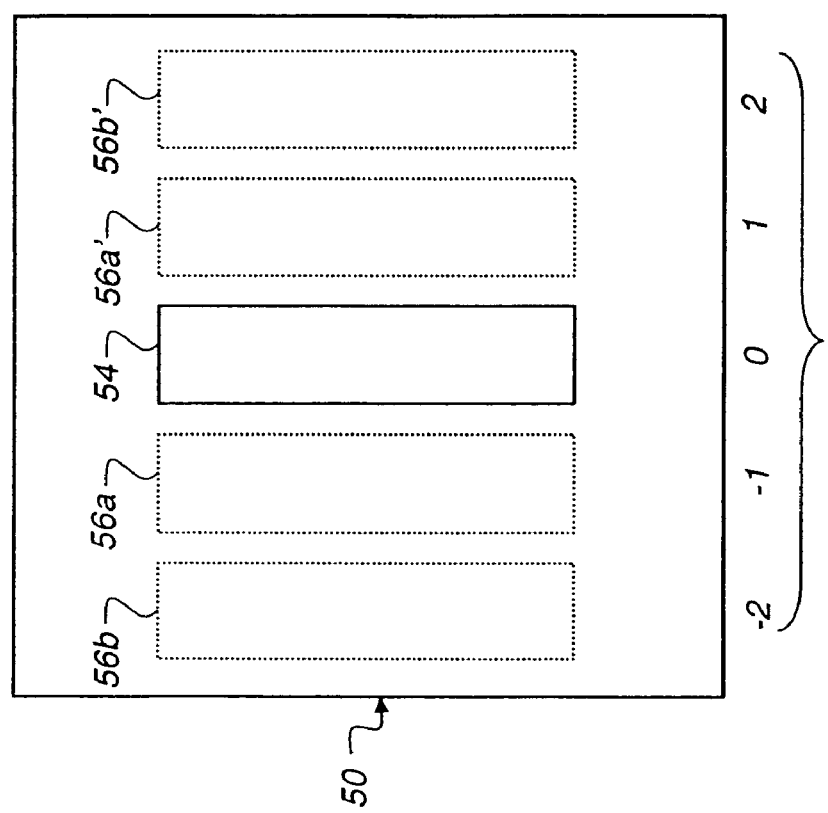
FIGS. 3A through 3C are plan views of a patterned mirror according to different embodiments of the present invention.

Patterned mirror 50, a type of light path selector, is preferably located near the common Fourier transform planes of lenses 26, 32, and 62, shown in FIG. 1. The design of patterned mirror 50, or an equivalent light path selector, depends on the type of light modulator that is employed for spectral switching. When using GEMS devices as optical switches 36a, 36b, and 36c, patterned mirror 50 can have the basic arrangement shown in FIG. 3A (not drawn to scale). Referring to FIGS. 1 and 3A, a central window 54 provides a transparent area that passes multispectral image-bearing light 28 as input toward lens 32. Lens 32 then directs this light, through dichroic X-cube 76, to optical switches 36a, 36b, and 36c. After modulation by optical switches 36a, 36b, and 36c, central window 54 transmits the zeroeth order reflected light back through patterned mirror 50 along optical axis O, shown in FIG. 1. Diffracted orders are incident on patterned mirror 50 as shown by dotted areas 56a, 56a', 56b, and 56b' which correspond to diffracted orders –1, 1, –2, and 2 in the exemplary embodiment shown in FIG. 3A. Of course, fewer or more diffracted orders could be reflected from patterned mirror 50 as desired. A cross-order and cleanup filter 52 can be provided in the embodiment of FIG. 1 to block any residual reflected and/or diffracted light from the imaging path. Techniques for cross-order suppression with GEMS devices are described, for example, in commonly assigned U.S. Pat. No. 6,678,085 entitled "High-Contrast Display System with Scanned Conformal Grating Device" to Kowarz et al.

Figure 3B:
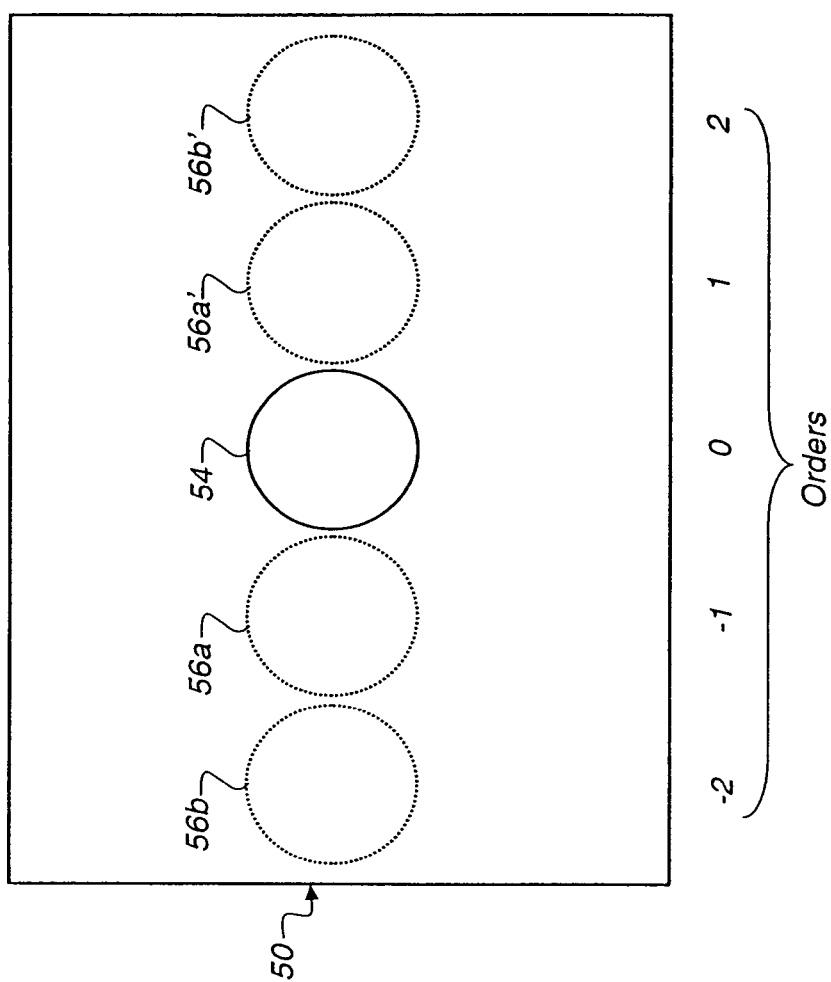
Figure 3C:
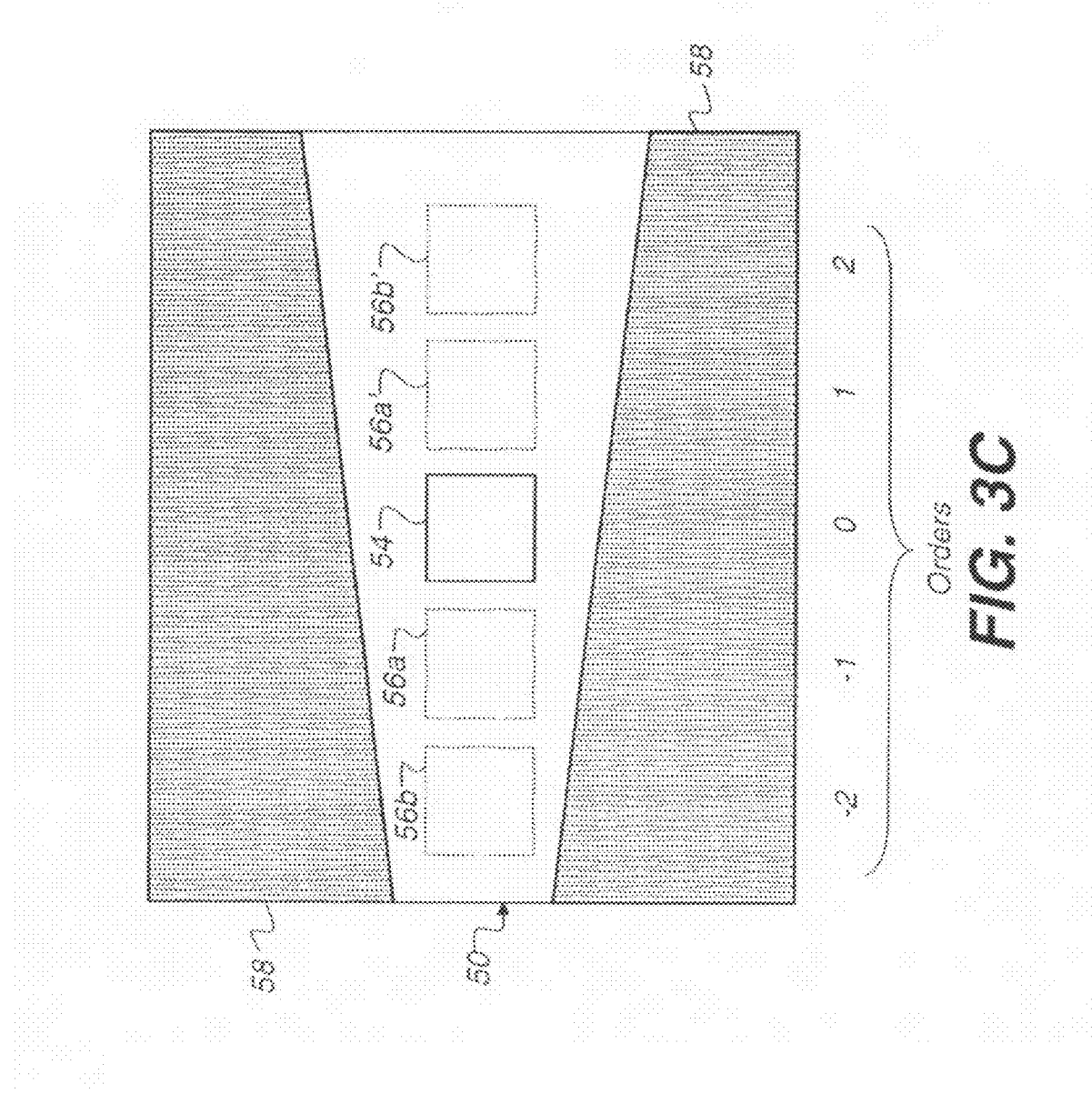

While FIG. 3A shows a rectangular shape for the transparent area of window 54 and for areas 56a, 56a', 56b, and 56b', in practice, this shape causes unequal f/# and MTF (Modulation Transfer Function) characteristics between horizontal and vertical axes. In order to provide more equal f/# along both axes, a circular opening for window 54 is preferred when possible, as shown in the example of FIG. 3B (not drawn to scale). Other modifications to patterned mirror 50 are also possible and may be advantageous, as shown in FIG. 3C (again, not drawn to scale). Here, window 54 and areas 56a, 56b, 56a', and 56b' are square and the surface of patterned mirror 50 is treated so that it is not fully reflective. Instead, opaque areas 58 are formed on patterned mirror 50 for absorbing cross-order light and blocking unwanted stray light from the imaging light path of switched spectral band light 44. Additional windows 54 may also be provided in patterned mirror 50 as needed.

Alternative Embodiments of Imaging Apparatus 10

Figure 4A:
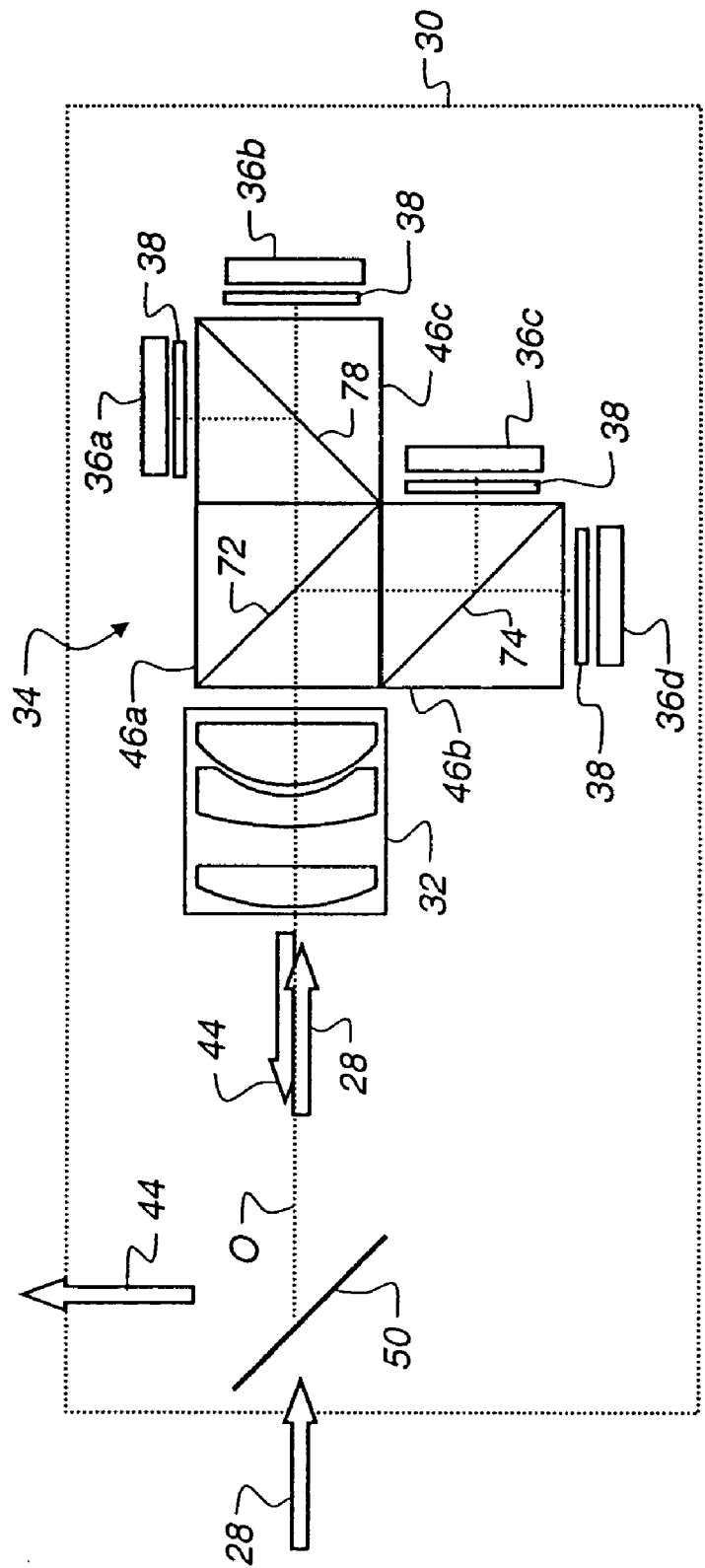
FIG. 4A is a schematic block diagram of a spectral band switching section in an embodiment with four spectral bands.

The basic scheme shown in FIG. 1 is followed in the alternative embodiments of FIGS. 4A, 4B, 5, 6, and 7, with additional wavelength bands provided, so that switched spectral band light 44 may be any of four, five, or six spectral bands respectively. Referring to FIG. 4A, dichroic separator 34 in spectral switching section 30 is a more complex assembly, having first, second, and third dichroic elements 46a, 46b, and 46c working in cooperation and acting as dichroic beamsplitters. By way of example, FIGS. 8A through 8D are graphs showing the transmittance and reflectance as a function of wavelength of various surfaces of first and second dichroic elements 46a and 46b. A dichroic surface 72 reflects lower wavelengths as shown by a curve 82' in FIG. 8A, sending the lower wavelengths towards dichroic element 46b and sending higher wavelengths towards dichroic element 46c. Dichroic surface 72 transmits higher wavelengths as shown by a curve 82" in FIG. 8C. In dichroic element 46b, a dichroic surface 74 reflects lower wavelengths towards optical switch 36c, as shown by a curve 84' in FIG. 8B, and transmits upper wavelengths towards optical switch 36d, as shown by a curve 84" in FIG. 8D. A dichroic surface 78 in dichroic element 46c behaves similarly.

Figure 4B:
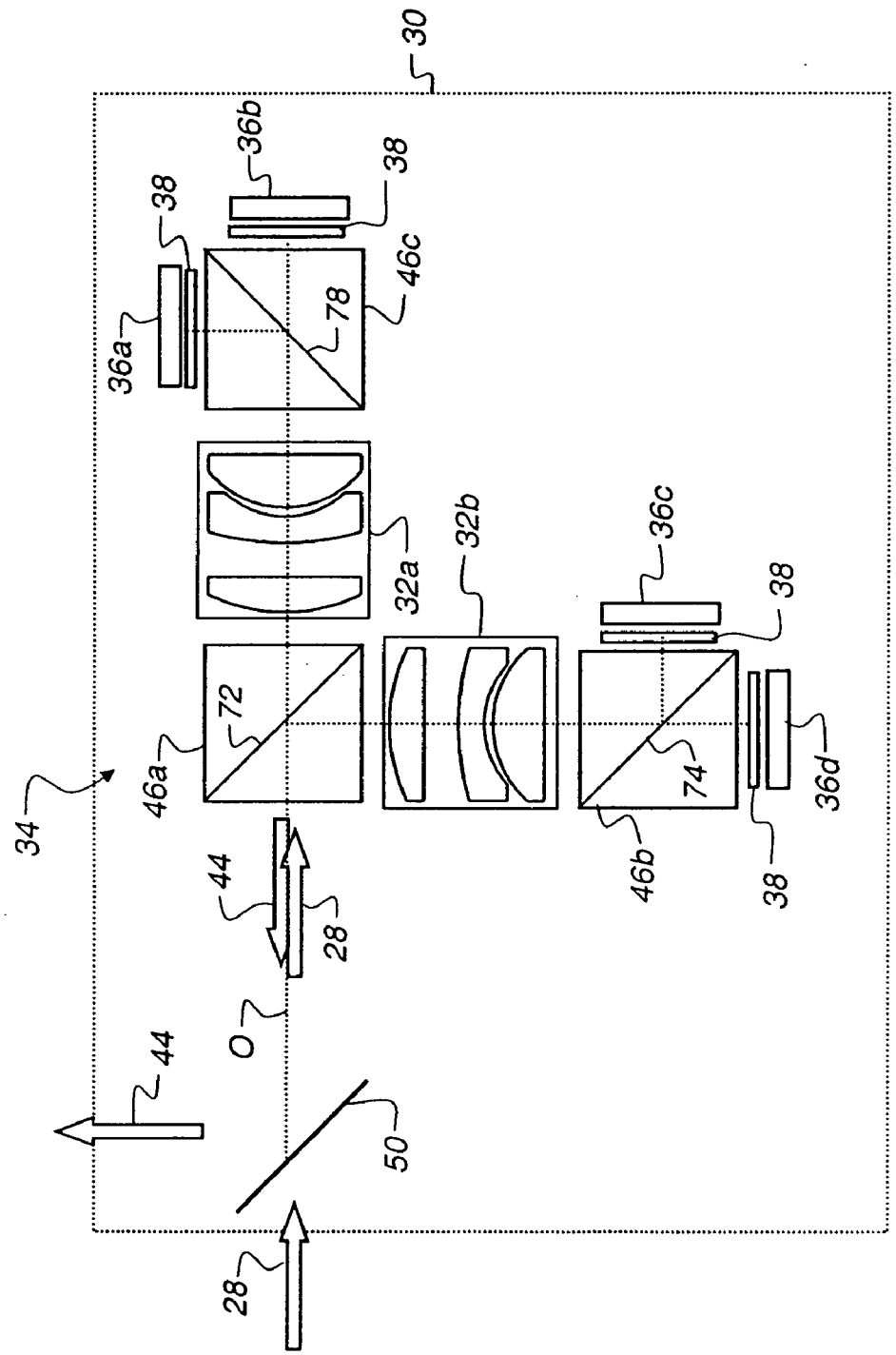
FIG. 4B is a schematic block diagram of a spectral band switching section in an alternative embodiment with four spectral bands.

FIG. 4B shows an alternative embodiment that enables better optimization of the imaging performance for each spectral band. Here, each dichroic element 46a, 46b, 46c again acts as a dichroic separator. Dichroic element 46a first splits the incoming light into two separate branches of components. One portion goes to lens 32a in a first branch and is then further split so that one spectral band goes to optical switch 36a and the other spectral band goes to optical switch 36b. Similarly, in a second branch off of dichroic element 46a, light goes to a lens 32b and is also split, with one spectral band of this light going to optical switch 36c and the other spectral band going to optical switch 36d. Using this arrangement, for example, dichroic element 46a directs blue and green wavelengths through lens 32a and red and near-IR wavelengths through lens 32b. Lenses 32a and 32b and other components in each branch can then be optimized for their respective wavelength bands.

Figure 5:
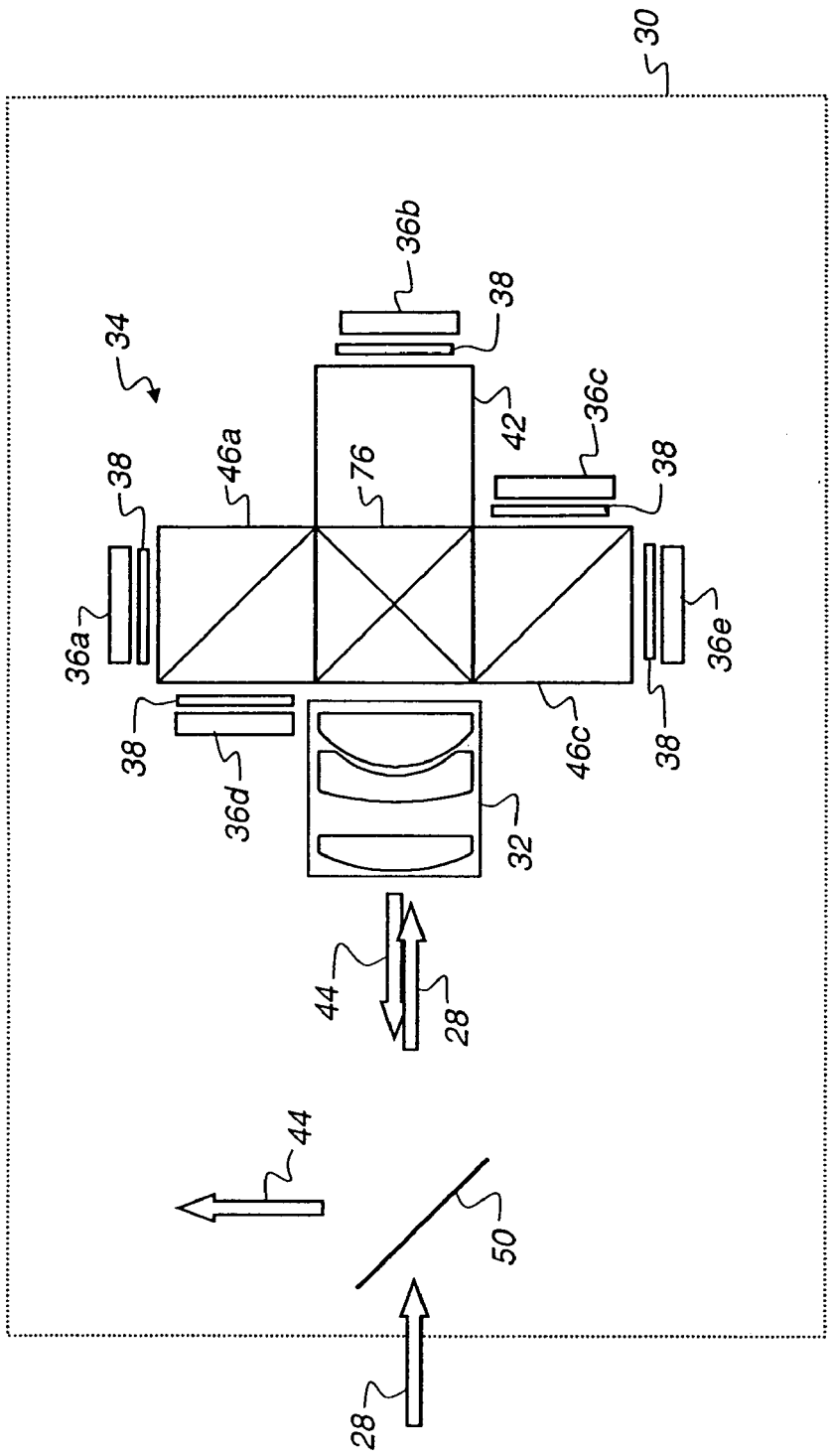
FIG. 5 is a schematic block diagram of a spectral band switching section in an embodiment with five spectral bands.
Figure 6:
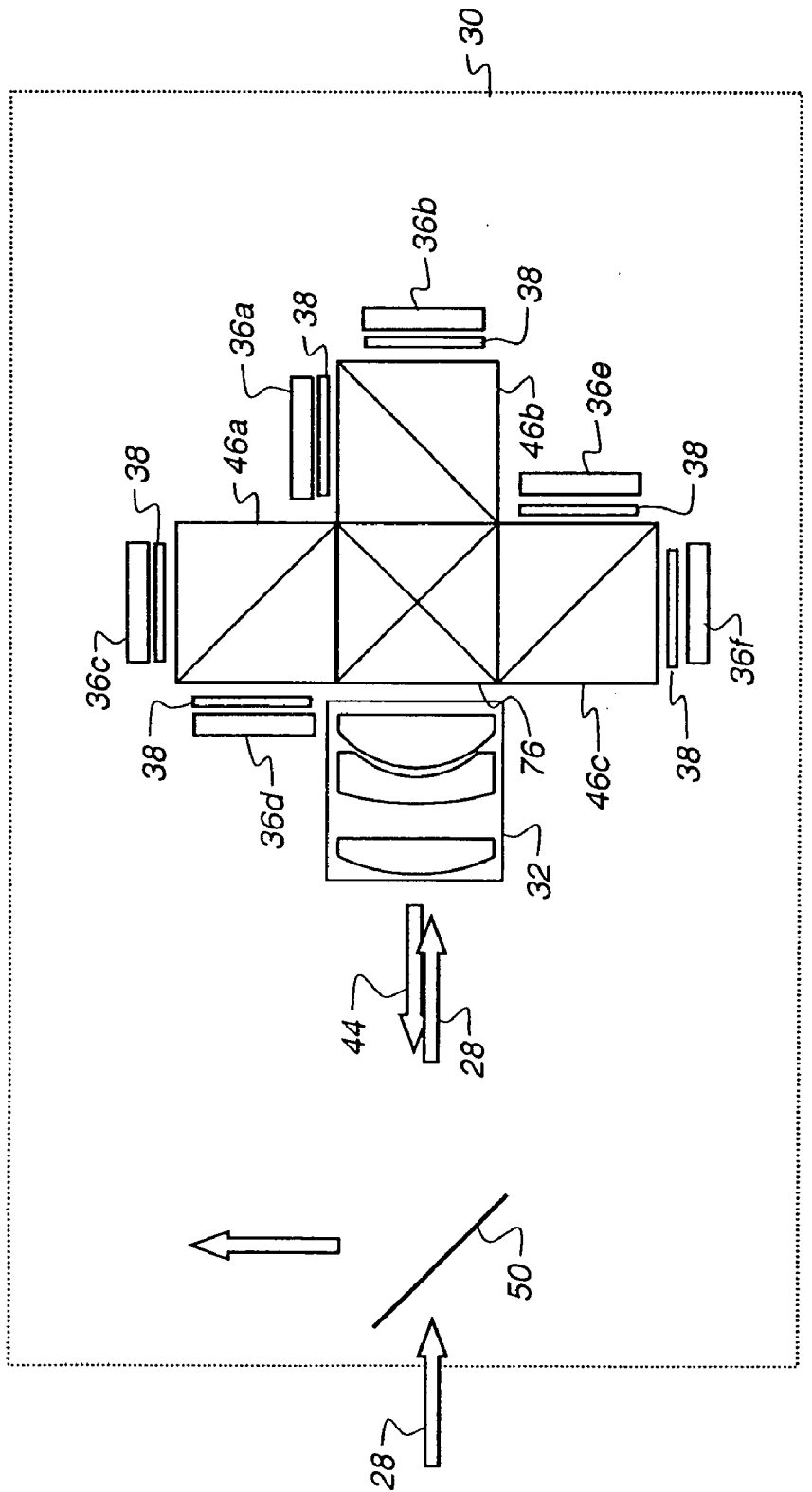
FIG. 6 is a schematic block diagram of a spectral band switching section in an embodiment with six spectral bands.

FIGS. 5 and 6 adapt the pattern described with reference to FIGS. 1 and 4A for embodiments with five and six optical switches, i.e., 36a, 36b, 36c, 36d, 36e, and 36f. An X-cube 76 provides an initial separation of wavelengths in these embodiments, supported by two or more dichroic elements 46a, 46b, and 46c. In the embodiment of FIG. 5, which enables selection of five spectral bands, an additional optical compensation element 42 is used to equalize the optical path length to optical switch 36b. For dichroic elements 46a and 46c that are, for example, dichroic cubes, the optical compensation element 42 can be a glass cube of the same optical length. The embodiment of FIG. 6 enables selection of six spectral bands, with each of the three bands of wavelengths emerging from X-cube 76 passing through a corresponding dichroic element 46a, 46b and 46c. One may observe that the alternative arrangement of FIG. 4B, with two or more lenses following the first dichroic separating component, is adaptable for the embodiments shown in FIGS. 1, 5, 6, and 7.

As is familiar to those skilled in the electronic imaging arts, light throughput from X-cube 76 is imperfect, as is shown in the graph of FIG. 9. In FIG. 9, curves 86', 86", and 86''' show the relative light transmission throughput for light wavelengths for the different color channels provided from a typical X-cube 76. Each curve 86', 86", and 86''' corresponds to a color channel. There is some overlap between transmission curves 86', 86", and 86''', which results in an amount of spectral crosstalk between channels. The embodiment of FIG. 7 employs a dichroic interleaver 40 as one alternative used to compensate for this crosstalk. X-cubes 76a and 76b exhibit different wavelength transmission characteristics in this embodiment. In addition to some amount of spectral crosstalk when using dichroic surfaces, there can also be some polarization-splitting effects, particularly at transitions between color channels. Dichroic interleaver 40 can also compensate for these effects.

Figure 7:
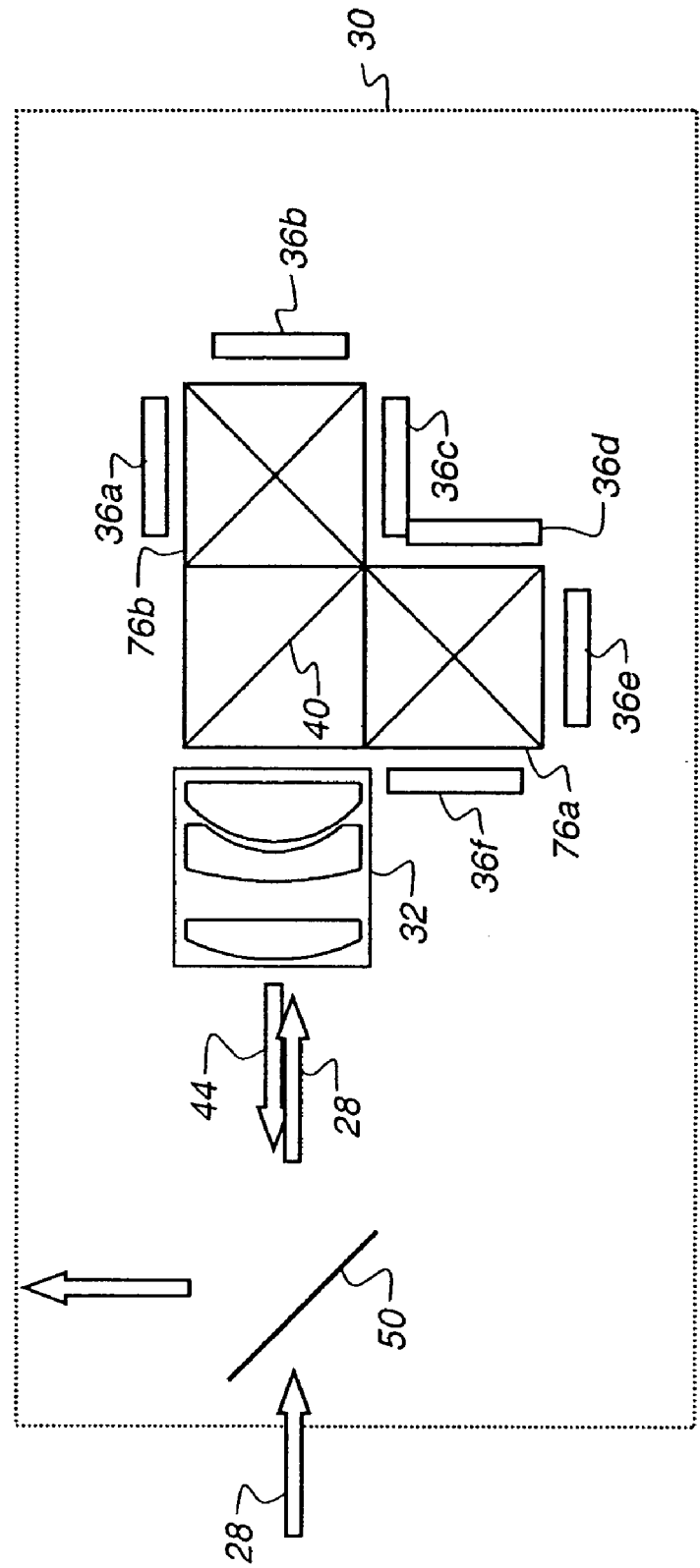
FIG. 7 is a schematic block diagram of a spectral band switching section in an embodiment with six spectral bands and a dichroic interleaver.

Referring to the graphs of FIGS. 10A and 10B, there are shown transmission and reflection behavior, respectively, for an ideal dichroic interleaver 40, shown, for example, in FIG. 7. FIG. 10A shows transmission curves 88', 88", and 88''' for dichroic interleaver 40 over a range of wavelengths. By way of comparison, transmission curves 86', 86", and 86''' of X-cube 76a are shown in dotted outline form, superimposed on transmission curves 88', 88", and 88''' for one side of dichroic interleaver 40. FIG. 10B shows the complementary reflection curves 98', 98", and 98''' for dichroic interleaver 40 that serve to filter light that is directed toward X-cube 76b. (Similar corresponding X-cube 76b also shown in FIG. 7 transmission curves could also be shown superimposed in FIG. 10B.) For dichroic interleaver 40, dichroic surfaces can be finely tuned to provide near-ideal performance as shown in the steep response curves of FIGS. 10A and 10B, using dichroic surfaces prepared by suppliers such as Semrock, Inc. of Rochester, N.Y. Although transmission curves for X-cubes 76, 76a, and 76b are imperfect, the spectral bands that are transmitted to optical switches 36a, 36b, 36c, 36d, 36e, and 36f have very sharp edges due to dichroic interleaver 40. The use of telecentric optics helps to simplify the design and fabrication of dichroic interleaver 40.

Figure 11:
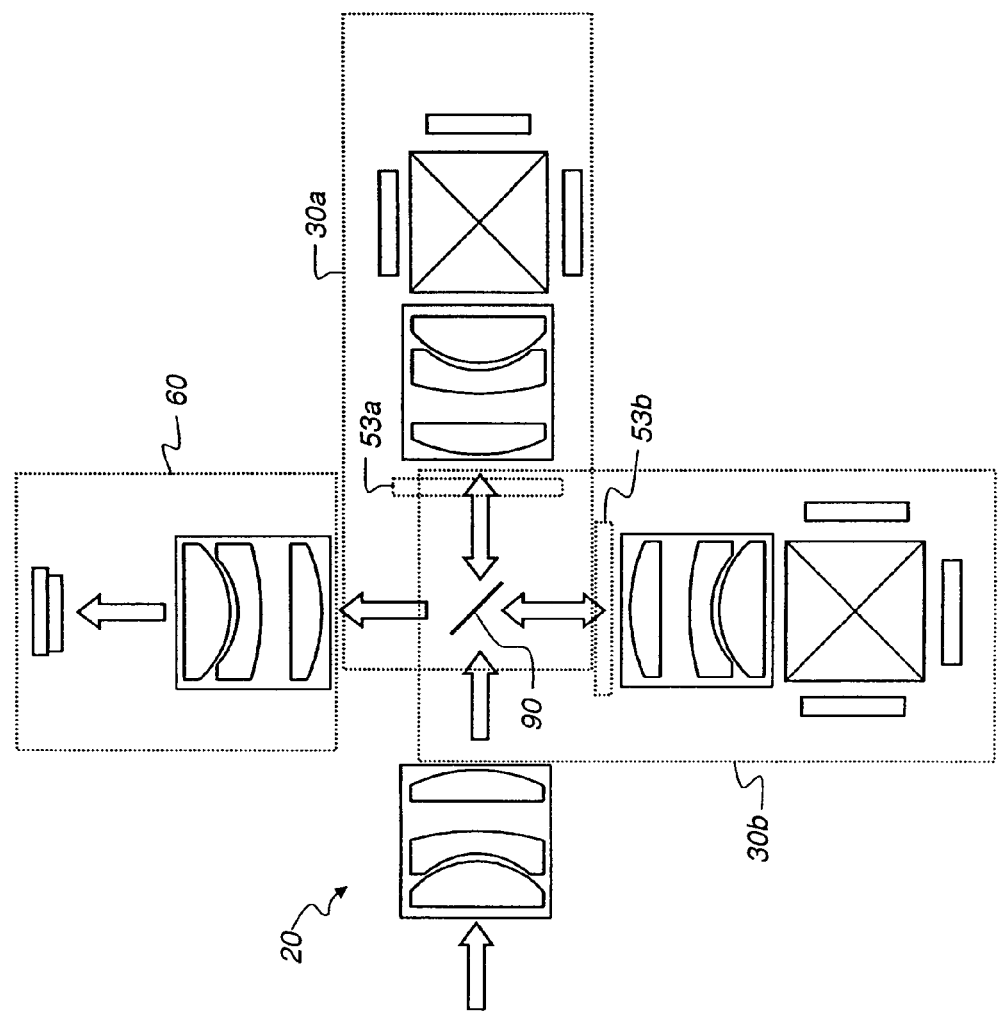
FIG. 11 is a schematic block diagram of a spectral imaging system according to an alternative embodiment of the present invention.
Figure 12:
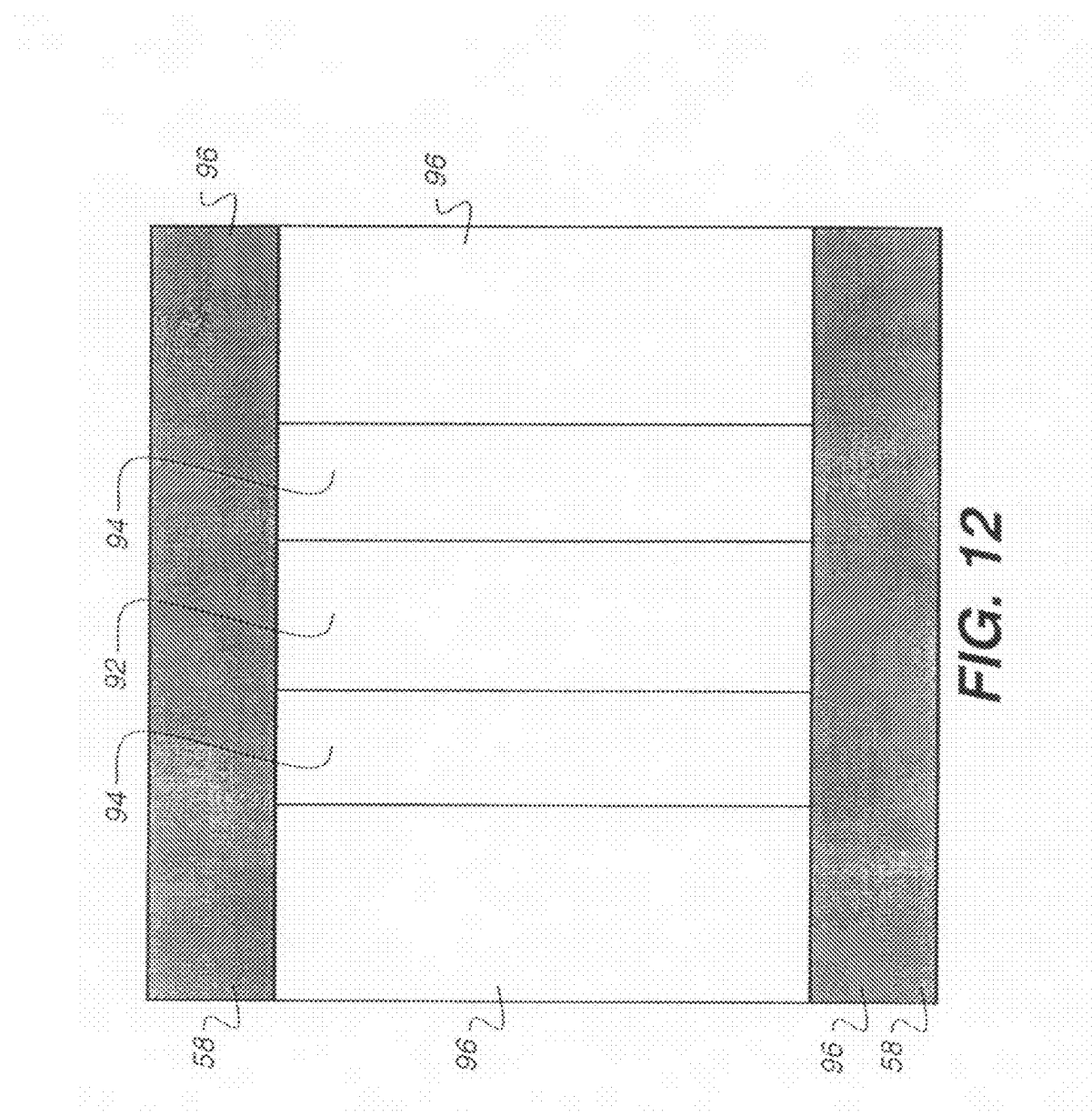
FIG. 12 is a plan view of a patterned dichroic element according to one embodiment of the present invention.

The basic arrangement of the preceding embodiments can also be extended to provide wideband imaging that might include light outside of the visible spectrum. For example, FIG. 1 could be adapted to provide spectral switching between three bands in the near-infrared region. Alternatively, two separated regions of the spectrum could be obtained. Referring to FIG. 11, there is shown one embodiment of imaging apparatus 10 having two spectral switching sections 30a and 30b. Here, spectral switching section 30a provides visible light while spectral switching section 30b provides light in the infrared spectrum. A patterned dichroic element 90 is substituted in place of patterned mirror 50 (previously shown in FIG. 1) as a suitable light path selector element to split visible light from the infrared light. Referring to FIG. 12, patterned dichroic element 90 in FIG. 11 has a number of different dichroic coatings, as follows:

(i) a central section 92 transmits visible light and reflects near IR;

(ii) a dichroic region 94 reflects both visible light and near IR; and (iii) a dichroic region 96 reflects visible light and transmits near IR.

Additionally in FIG. 11, clean up filters 53a and 53b are provided to eliminate IR light from visible light spectral switching section 30a and to block visible light from IR light spectral switching section 30b.

With this arrangement in FIG. 11, visible input light is transmitted to visible light spectral switching section 30a by dichroic section 92 and near IR is reflected to IR light spectral switching section 30b by both dichroic regions 92 and 94. Zeroeth order reflected light (that is, undiffracted light) returning from both visible light spectral switching section 30a and IR light spectral switching section 30b is sent back toward input optics section 20. Diffracted orders from visible light spectral switching section 30a are reflected toward image forming section 60 by dichroic regions 94 and 96. Similarly, diffracted orders from IR light spectral switching section 30b are transmitted towards image forming section 60 through dichroic region 96.

It can be further observed that the arrangement of FIG. 11 could be similarly employed for switching light from the visible spectrum or from any suitable portion of the spectrum, so that both spectral switching sections 30a and 30b could be used for visible light or for light over any suitable portion of the spectrum. Other arrangements of patterned dichroic element 90 could also be used, depending on the desired spectral ranges. Furthermore, larger numbers of spectral bands can be obtained by incorporating, into the spectral switching sections of FIG. 11, the approaches shown in the examples of FIGS. 4 through 7.

Figure 15:
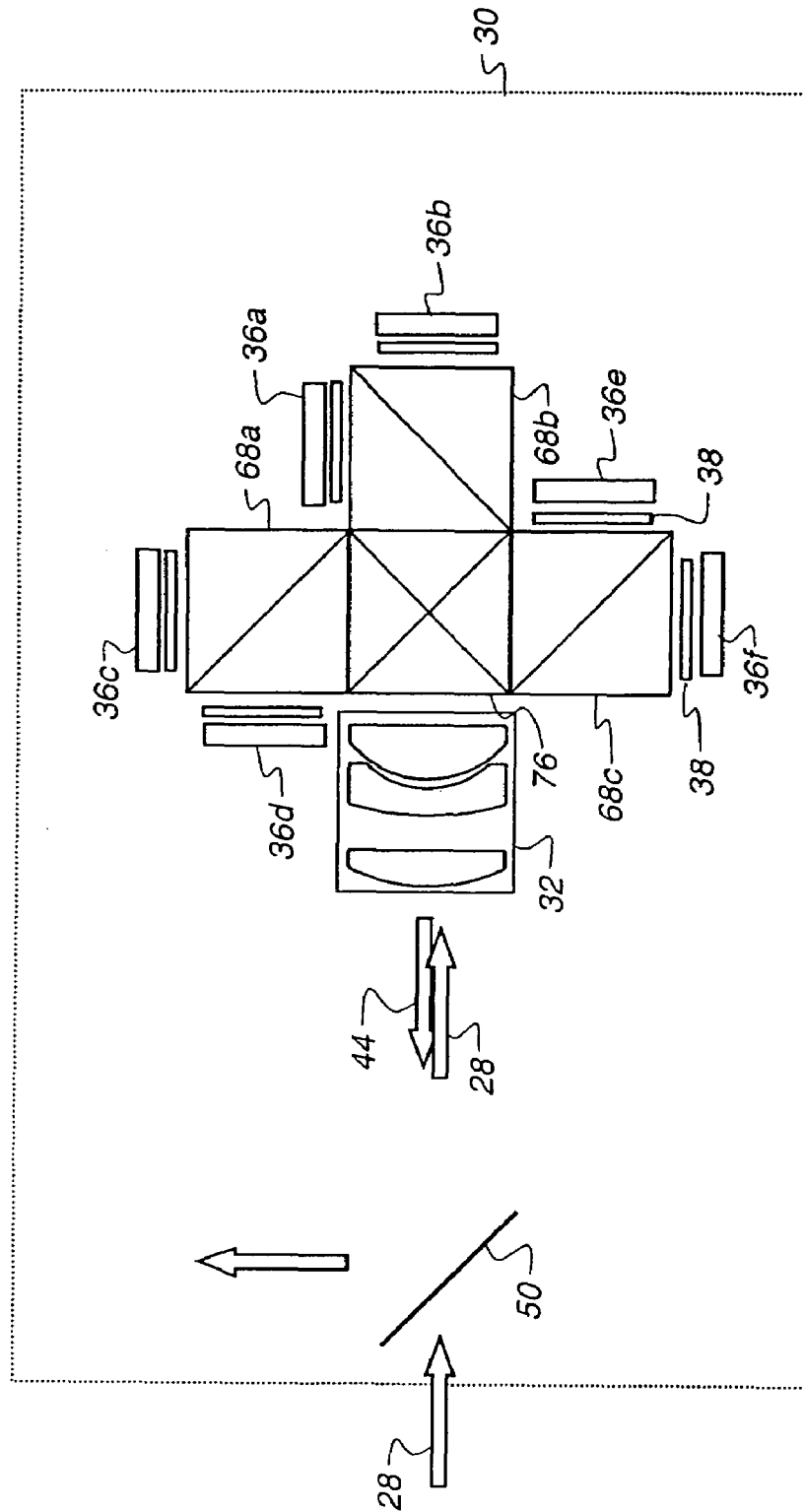

The preceding embodiments can be modified to provide spectral band imaging coupled with polarization selection. Referring to FIG. 15, there is shown a polarimetric spectral imaging system with an arrangement similar in appearance to the FIG. 6 configuration, using polarization beamsplitters 68a, 68b, 68c in the various spectral imaging channels. With this arrangement, X-cube 76 separates light into one of three channels, by wavelength. In one channel, for example, optical switches 36c and 36d each modulate light having a different polarization state, with separation of these states performed by polarization beamsplitter 68a. This same approach can be adapted for imaging two or more spectral bands.

The GEMS device is well-suited as a type of programmable optical switch 36a, 36b, 36c for imaging apparatus 10. As described in the '663 Kowarz et al. patent cited earlier, GEMS design allows any number of elongated ribbon elements to be incorporated in a device and permits a wide range of ribbon element lengths, with any suitable number of intermediate supports provided for each ribbon and with any number of adjacent ribbons electrically coupled to act in unison. This inherent flexibility allows the GEMS device to be scaled so that each individual addressable active area can have an optimal size for its application. For spectral imaging, for example, an addressable active area in excess of 1 cm$^2$ could be activated at one time, with a relatively high fill factor. To size a GEMS device appropriately requires selection of suitable ribbon lengths, support structures and dimensions, and of other known parameters, as would be apparent to one skilled in the micromechanical fabrication arts.

Figure 13C:
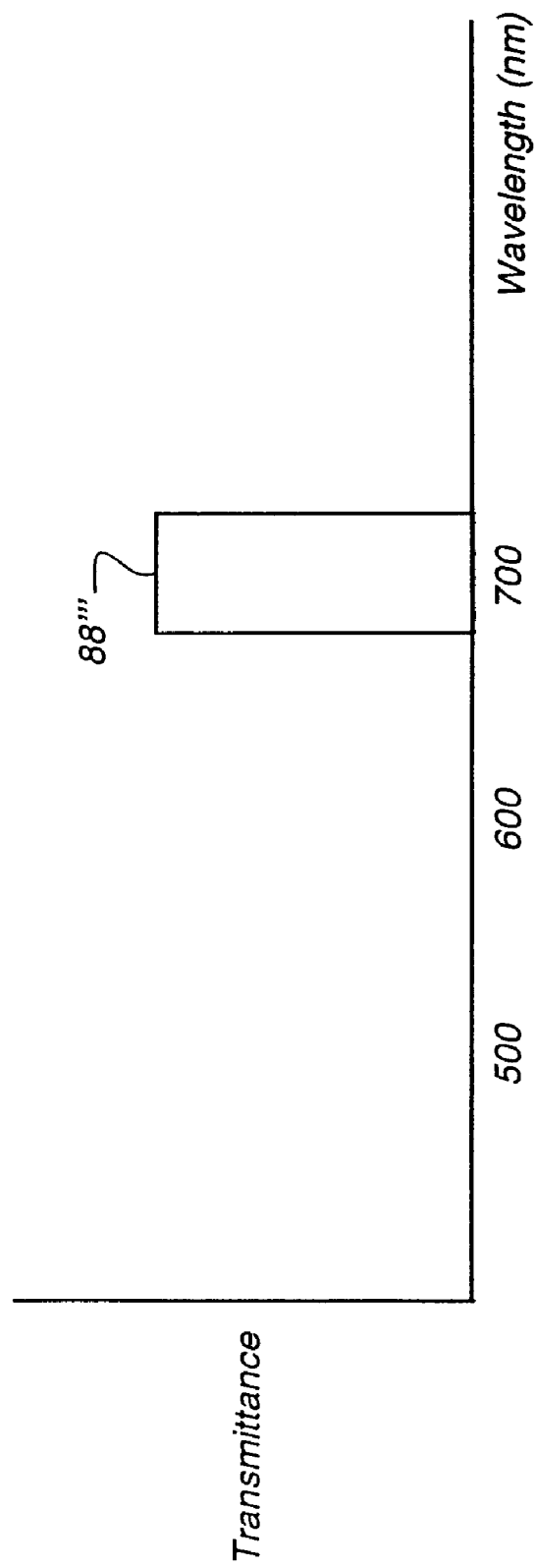

In one embodiment, optical switches 36a, 36b, 36c are synchronously and repeatedly enabled and disabled to obtain spectral bands in a time-sequential fashion. This timing pattern is shown in simplified form in the sequence of FIGS. 13A, 13B, and 13C. For example, a first spectral band centered at a wavelength of 500 nm could be captured as shown by transmission curve 88' in FIG. 13A. This is followed by capture of a second spectral band centered at 600 nm as shown by transmission curve 88'' in FIG. 13B. A third spectral band centered at 700 nm is then captured as shown by transmission curve 88''' in FIG. 13C. Using this sequential approach, equal time periods could be allocated for the capture of each sequential spectral band. Alternatively, one or more of these time periods could be adjusted to be unequal to the others, such as when the relative sensitivity of image sensor 64 is wavelength-dependent, for example.

Individual optical switches 36a, 36b, 36c, etc. could be activated for spectral band capture at the same time, or singly, or in pairs or groups of more than two at a time for obtaining different types of images. One or more of optical switches 36a, 36b, 36c, etc. could be selectively disabled for obtaining various types of images.

Simultaneous capture by two or more optical switches 36a, 36b, 36c, etc. could allow the sensing of a spectral signature. The capture of three or more spectral bands simultaneously could also provide an improved signal-to-noise ratio when used in conjunction with Hadamard transform techniques. In such an approach, each captured image data set is processed using Hadamard transform and S-matrix techniques familiar to those skilled in the spectral imaging arts. One example of Hadamard transform utilization is given by R. A. DeVerse, R. M. Hammaker, and W. G. Fateley in an article entitled "Realization of the Hadamard Multiplex Advantage Using a Programmable Optical Mask in a Dispersive Flat-Field Near-Infrared Spectrometer" *Applied Spectroscopy*, vol. 54 no. 12, pp. 1751-1758.

Figure 14A:
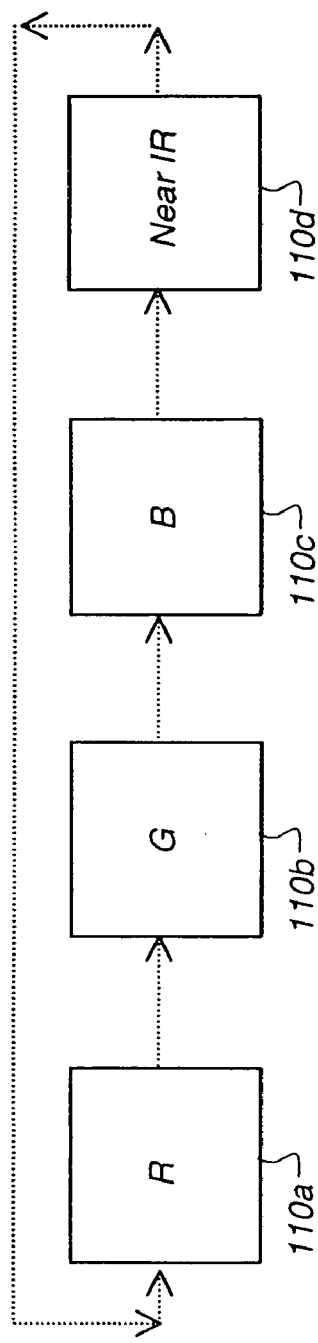
FIGS. 14A through 14E show exemplary sequences that can be employed for imaging a standard set of spectral bands over time; and, FIG. 15 is a schematic block diagram of a spectral band switching section in a spectral polarimetric embodiment.
Figure 14B:
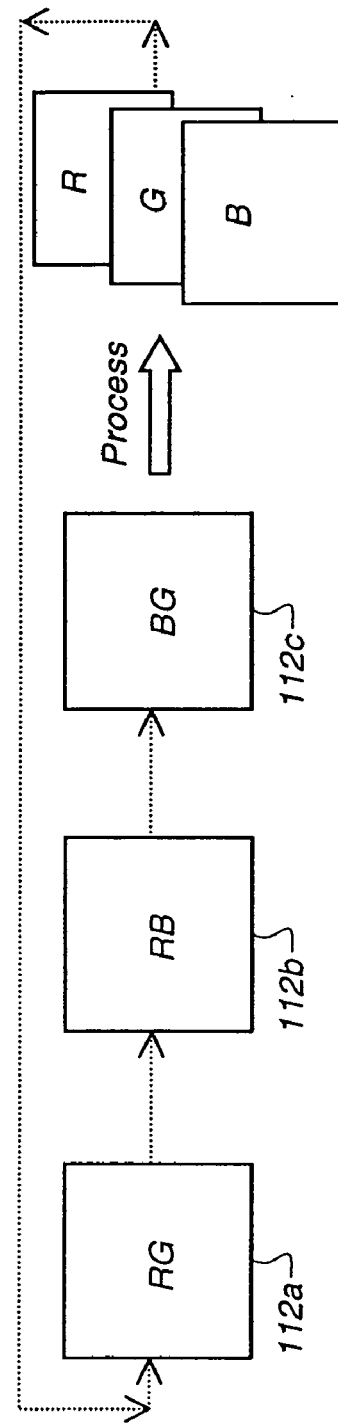

FIGS. 14A through 14E show different timing sequences that can be employed for imaging a standard set of spectral bands over time. In FIG. 14A, the sequence of operation is shown by which, at successive times, imaging apparatus 10 captures a red image segment 110a, then a green image segment 110b, then a blue image segment 110c, then a near-IR image segment 110d. Each image segment 110a, 110b, 110c, 110d is some portion of the object field, which may be one or more lines or a larger area, possibly even the full object field at the capture wavelength. In FIG. 14B, the sequence of operation suitable for Hadamard transform processing is shown for a simple three-spectral-band system. Here, red and green spectral bands are captured at the same time in an image segment 112a. Next, red and blue spectral bands are captured in an image segment 112b. Lastly, blue and green spectral bands are captured in an image segment 112c. Again, each image segment 112a, 112b, 112c is some portion of the object field, which may be one or more lines or a larger area, possibly the full object field at the capture wavelength. Processing of these paired spectral bands using Hadamard transform techniques then yields RGB data for the full image field as represented in FIG. 14B.

The spatial light modulators that serve as optical switches 36a, 36b, 36c, can readily be configured, by control logic, to have multiple portions, each portion capable of being modulated independently of the others. At a minimum, there would be a first portion and a second portion such that the first portion can be modulated independently of the second portion and vice versa.

Figure 14C:
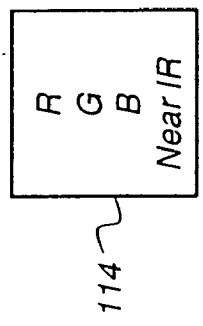
Figure 14D:
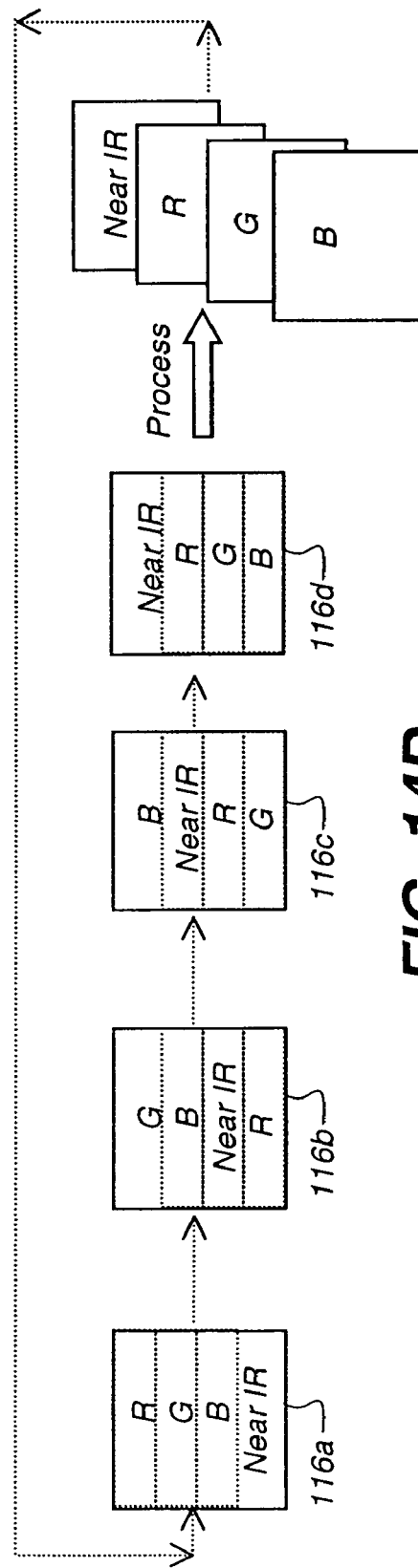

FIG. 14C shows an image segment 114 in which four spectral bands are captured simultaneously on the detector array of image sensor 64 using this approach. FIG. 14D shows a scrolling sequence of image segments 116a, 116b, 116c, 116d in which fractional portions of different spectral bands are switched to be captured at the same time. A scrolling sequence is followed with this technique, so that different portions of the image field are sensed at successive times using optical switches 36a-36d. This arrangement provides a type of scrolling programmable color filter array.

Referring back to FIG. 4A, for example, the sequence shown in FIG. 14C could be obtained using four optical switches 36a, 36b, 36c, and 36d. Multispectral image bearing light 28 shown in FIG. 4A is separated into four discrete image-bearing spectral bands, each directed to one of the four optical switches 36a, 36b, 36c, and 36d. As an example color-to-device mapping, a blue image-bearing spectral band goes to optical switch 36a, a green image-bearing spectral band goes to optical switch 36b, a red image-bearing spectral band goes to optical switch 36c, and a near-IR image-bearing spectral band goes to optical switch 36d. At one point in time, this arrangement can be used to obtain image segment 116a in FIG. 14D. To capture image segment 116a using a system with this example color-to-device mapping, the top portion of image segment 116a (labeled R) is switched by enabling a corresponding portion of optical switch 36c. Similarly, the adjacent portion of image segment 116a (labeled G) is switched by enabling a corresponding portion of optical switch 36b. Likewise, portions labeled B and Near-IR are obtained by enabling corresponding portions of optical switches 36a and 36d, respectively.

To capture image segment 116b in FIG. 14D, the corresponding enabled portions of optical switches 36a, 36b, 36c, and 36d (from FIG. 4A) are shifted. Likewise, additional shifts occur to obtain image segments 116c and 116d. This scrolling color array arrangement may be advantageous for some applications, such as where relative movement between the imaged object and imaging apparatus 10 is a factor. Because there are typically many independently addressable portions of optical switches 36a, 36b, 36c, and 36d, the scrolling sequence of the programmable color filter array can be made to appear very nearly continuous.

Figure 14E:
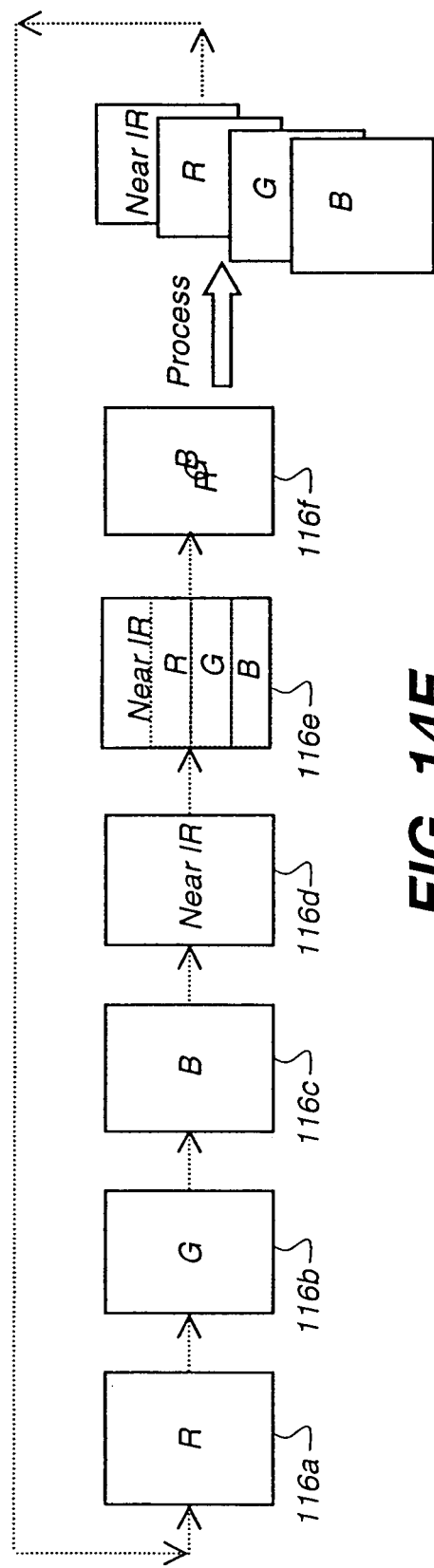

FIG. 14E shows yet another possible image capture sequence that could be used. Here, portions of Red, Green, and Blue image content are successively obtained, followed by near IR light. A scrolling sampling is then taken at image segment 116e, possibly reproducing the full sequence of FIG. 14D. Then, a panchromatic is obtained as image segment 116f, during which all spectral fields are switched on simultaneously to provide image data. As FIG. 14E suggests, any number of variations are possible depending on the imaging application. For example, there may be sequences that are optimized for obtaining spectral information from fast-moving objects or other sequences best used where it is advantageous to scan the image field slowly in order to obtain the maximum amount of data. Moreover, because the timing of optical switch 36a-36f actuation is programmable, different sequences may be used depending on the type of imaging needed at any particular moment.

As has been described with reference to FIGS. 14A-14E, it is possible to sample the image field at different wavelengths at different times. In some imaging applications, this may be advantageous, enabling various types of information to be obtained. There may be data such as luminance information that is available, at least at some level, over any of a number of spectral bands, for example.

Thus, the method and apparatus of the present invention can provide a programmable color filter array for directing light to an image sensor, or, more broadly, to a light-receiving device.

In the apparatus of the present invention, the different spectral bands directed to each optical switch 36a, 36b, 36c, etc. are preferably sharply defined and discrete, so that there would be no overlap, or only a minimal amount of overlap, between any two spectral bands that are modulated.

Alternative Embodiment Using Inverted Patterned Mirror 50

FIGS. 1, and 4-7 show embodiments in which patterned mirror 50 is generally arranged with window 54 being transmissive, as was described with reference to FIGS. 3A-3C. The balance of patterned mirror 50 is wholly, or at least largely, reflective in these embodiments. However, the arrangement of patterned mirror 50 could be inverted in an alternative embodiment using GEMS devices as optical switches 36a, 36b, 36c, with the corresponding repositioning of input optics section 20 and image forming section 60. That is, window 54 of patterned mirror 50 could be reflective, with the balance of patterned mirror 50 as wholly or largely transmissive. With reference to the arrangement of FIG. 1, the relative positions of input optics section 20 and image forming section 60 would then be interchanged, so that multispectral image bearing light 28 would be reflected toward spectral switching section 30 (rather than transmitted as in FIG. 1). Modulated light from spectral switching section 30 would then be transmitted (as diffracted orders from the GEMS device) through this inverted patterned mirror 50 as switched spectral band light 44 and directed to image forming section 60.

The invention has been described in detail with particular reference to certain preferred embodiments thereof; but it can be understood that variations and modifications can be effected within the spirit and scope of the invention. For example, while GEMS devices are particularly advantaged as optical switches due to high switching speeds, excellent contrast, and high fill factor, other types of spatial light modulators could be suitably deployed as optical switches 36a, 36b, 36c, etc. For example, reflective LCOS (Liquid Crystal On Silicon) devices could be used as optical switches 36a, 36b, 36c. Digital Micromirror Devices (DMDs), could also be employed, although contrast would not be optimal. The spatial light modulator used could be an area type, such as the LCOS or DMD devices, or could be a linear type, such as a linear GEMS or Grating Light Valve (GLV) device. The image data obtained could be made available for display, printing, or analysis. There are a considerable number of possible arrangements for supporting optics, including multi-component lenses, filters, polarizers, analyzers, apertures, compensators, etc. While the embodiments described hereinabove employ patterned mirror 50 as the light path selector element, other types of devices could be used for performing this function, including a polarization beamsplitter for a reflective LCD device or a Total Internal Reflection (TIR) prism for a DMD device or other type of micromirror device.

PART LIST

10. Imaging apparatus
20. Input optics section
22. Forward optics
24. Intermediate image
26. Lens
28. Multispectral image bearing light
30, 30a, 30b. Spectral switching section
32, 32a, 32b. Lens
34. Dichroic separator
35a, 35b. Dichroic plate
36a, 36b, 36c, 36d, 36e, 36f Optical switch
37. Philips prism 38. Filter
40. Dichroic interleaver
42. Optical compensation element
44. Switched spectral band light
46a, 46b, 46c. Dichroic element
50. Patterned mirror
52. Filter
53a, 53b Filter
54. Window
56a, 56b, 56a', 56b'. Areas
58. Opaque area
60. Image forming section
62. Lens
64. Image sensor
68a, 68b, 68c. Polarization beamsplitter
70. Control logic processor
72, 74, 78. Dichroic surface
76, 76a, 76b. X-cube
82', 82", 84' 84". Curve
86', 86", 86'" Transmission curve
88', 88", 88'" Transmission curve
90. Patterned dichroic element
92, 94, 96. Dichroic region
98', 98", 98'" Reflection curve
110a, 110b, 110c, 110d. Image segment
112a, 112b, 112c. Image segment
114. Image segment
116a, 116b, 116c, 116d, 116e, 116f Image segment

What is claimed is:

1. An imaging apparatus comprising:
   a) an input optics section for obtaining a multispectral image bearing light;
   b) a programmable spectral switching section comprising:
   a first lens for directing light along toward a dichroic separator, the dichroic separator separating the multispectral image bearing light into a plurality of discrete spectral bands, each spectral band directed to one of a plurality of optical switches to form a one-to-one correspondence;
   each optical switch in the plurality of optical switches is selectively enabled to redirect its corresponding spectral band as switched spectral band light;
   a light path selector element directing the switched spectral band light toward an image forming section;
   c) the image forming section comprising a sensor lens for directing the switched spectral band light toward an image sensor;
   the image sensor forming image data according to the switched spectral band light from each optical switch; and,
   d) a control logic processor in communication with the optical switches and with the image sensor, the control logic processor providing instructions for enablement of the optical switches and obtaining sensor data.

2. The imaging apparatus according to claim 1 wherein the light path selector element comprises a patterned mirror.

3. The imaging apparatus according to claim 1 wherein the light path selector comprises a patterned dichroic element.

4. The imaging apparatus according to claim 2 wherein the patterned mirror comprises a reflective aperture positioned along the optical axis and a transparent surface area.

5. The imaging apparatus according to claim 3 wherein the transparent area is substantially circular in shape.

6. The imaging apparatus according to claim 1 wherein the light path selector element comprises at least one opaque area.

7. The imaging apparatus according to claim 1 wherein the optical switch is a GEMS device.

8. The imaging apparatus according to claim 1 wherein the optical switch is an LCOS light modulator.

9. The imaging apparatus according to claim 1 wherein the optical switch is a digital micromirror device.

10. The imaging apparatus according to claim 1 wherein the dichroic separator is selected from the group consisting of an X-cube, a Philips prism, and dichroic plates.

11. The imaging apparatus according to claim 1 wherein the optical switch generates one or more diffracted orders of light.

12. The imaging apparatus according to claim 1 further comprising a polarization beamsplitter in the path of at least one spectral band.

13. The imaging apparatus according to claim 1 wherein the plurality of spectral bands comprises three or more spectral bands.

14. The imaging apparatus according to claim 1 wherein each optical switch has at least a first addressable portion and a second addressable portion that are modulated independently of each other.

15. The imaging apparatus according to claim 1 wherein the first lens is telecentric.

16. The imaging apparatus according to claim 1 wherein the dichroic separator also recombines light from the plurality of optical switches to form the switched spectral band light.

17. The imaging apparatus according to claim 1 wherein the switched spectral band light passes back through the first lens.

18. An imaging apparatus comprising:
   a) an input optics section for obtaining a multispectral image bearing light;
   b) a programmable spectral switching section comprising:
   a first lens that directs the multispectral image bearing light toward a dichroic separator,
   the first lens cooperating with the dichroic separator to form a plurality of discrete spectral band images,
   wherein each spectral band image is formed near a corresponding optical switch;
   each corresponding optical switch is selectively enabled to redirect at least a portion of its spectral band image back through the dichroic separator and toward a light path selector element,
   wherein the light path selector element directs the spectral band image from each corresponding optical switch to an image forming section;
   c) the image forming section comprising a sensor lens for directing the image from each corresponding optical switch toward an image sensor;
   the image sensor forming image data according to the spectral band image from each corresponding optical switch; and,
   d) a control logic processor in communication with the optical switches and with the image sensor, the control logic processor providing instructions for enablement of the optical switches and obtaining sensor data.

19. The imaging apparatus of claim 18 wherein the input optics section forms an intermediate image.

20. The imaging apparatus of claim 18 wherein the light path selector element is disposed near the Fourier transforms plane of the first lens.

21. The imaging apparatus of claim 18 further comprising at least one clean-up optical filter for the spectral band image from each optical switch.

22. The imaging apparatus of claim 18 wherein the light path selector element comprises a patterned mirror.

23. The imaging apparatus of claim 18 wherein the first lens is telecentric.

24. The imaging apparatus of claim 18 wherein the optical switches are GEMS devices.

25. A method for imaging comprising:
   a) gathering a multispectral image bearing light;
   b) separating the multispectral image bearing light into at least two discrete spectral bands;
   c) directing the at least two discrete spectral bands to at least two optical switches;
   d) selectively enabling at least one of the at least two optical switches, so that each enabled optical switch modulates at least a portion of its corresponding discrete spectral band to form modulated spectral band light;
   e) recombining the modulated spectral band light from the at least two optical switches to form a recombined switched spectral band light;
   f) directing the recombined switched spectral band light toward an image sensor; and
   g) generating image data according to the recombined switched spectral band light.

26. The method of claim 25 wherein the step of directing the at least two discrete spectral bands comprises forming an image near the at least two optical switches.

27. The method of claim 25 wherein the step of separating the multispectral image bearing light into at least two discrete spectral bands comprises directing the multispectral image bearing light through a dichroic separator.

28. The method of claim 25 wherein the step of separating the multispectral image bearing light into at least two discrete spectral bands comprises directing the light through either an X-cube or a group of dichroic plates or a Philips prism.

29. The method of claim 27 wherein the step of recombining the switched spectral band light comprises directing the light through the dichroic separator.

30. The method of claim 25 wherein the step of selectively enabling at least one of the optical switches generates diffracted orders of light.

31. The method of claim 25 wherein the step of selectively enabling the optical switches is done in a sequence such that image data over a plurality of spectral bands is obtained simultaneously.

32. The method of claim 25 wherein a first portion of an object field is imaged over a first discrete spectral band and a second portion of the object field is imaged over a second discrete spectral band.

33. The method of claim 32 wherein, at a later moment, the first portion of the object field is imaged over the second discrete spectral band.

34. A method for providing a programmable color filter array, comprising:
   a) forming a programmable spectral filter comprising a spectral band separator and at least a first optical switch, a second optical switch, and a third optical switch;
   b) directing a multispectral image bearing light to the programmable spectral filter;
   c) enabling a segment of the first optical switch to direct a first portion of the image-bearing light, in a first spectral band, toward a light-receiving device;
   d) enabling a segment of the second optical switch to direct a second portion of the image-bearing light, in a second spectral band, toward the light-receiving device; and
   e) enabling a segment of the third optical switch to direct a third portion of the image-bearing light, in a third spectral band, toward the light-receiving device.

35. The method of claim 34 wherein steps c), d), and e) are performed simultaneously.

36. The method of claim 34 wherein the light-receiving device is an image sensor.

37. The method of claim 34 wherein the first spectral band is red, the second spectral band is green and the third spectral band is blue.

* * * * *